(12) United States Patent
Scholl et al.

(10) Patent No.: US 7,670,776 B1
(45) Date of Patent: Mar. 2, 2010

(54) MYH GENE VARIANTS AND USE THEREOF

(75) Inventors: Thomas Scholl, W. Borough, MA (US); Kristilyn Eliason, Salt Lake City, UT (US); Thaddeus S. Judkins, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 59 days.

(21) Appl. No.: 11/781,131

(22) Filed: Jul. 20, 2007

Related U.S. Application Data

(63) Continuation-in-part of application No. 11/187,670, filed on Jul. 22, 2005, now Pat. No. 7,563,571.

(60) Provisional application No. 60/832,387, filed on Jul. 21, 2006, provisional application No. 60/673,441, filed on Apr. 21, 2005, provisional application No. 60/621,298, filed on Oct. 22, 2004, provisional application No. 60/590,319, filed on Jul. 22, 2004.

(51) Int. Cl.
*C12Q 1/68* (2006.01)

(52) U.S. Cl. ......................................... 435/6

(58) Field of Classification Search ....................... None
See application file for complete search history.

(56) References Cited

U.S. PATENT DOCUMENTS

| | | | |
|---|---|---|---|
| 6,013,473 A * | 1/2000 | Wei ........................... | 435/69.1 |
| 6,051,222 A | 4/2000 | Wei | |
| 6,639,063 B1 | 10/2003 | Edwards et al. | |

FOREIGN PATENT DOCUMENTS

| | | |
|---|---|---|
| WO | WO 97/33903 | 9/1997 |
| WO | WO 03/014390 | 2/2003 |

OTHER PUBLICATIONS

Slupska et al. ("Cloning and sequencing a human homolog (hMYH) of the *Escherichia coli* mutY gene whose function is required for the repair of oxidative DNA damage." J Bacteriol. Jul. 1996;178(13):3885-92).*
Lucentini et al (The Scientist (Dec. 2004) vol. 18).*
Wacholder et al (J. Natl. Cancer Institute (2004) 96(6):434-442).*
Al-Tassan et al., "Inherited variants of MYH associated with somatic G:C→T:A mutations in colorectal tumors", *Nature Genetics*, Feb. 2002, 30:227-232.

Audebert et al., "Effect of single mutations in the OGG1 gene found in human tumors on the substrate specificity of the Ogg1 protein", *Nucleic Acids Research*, 2000, 28(14):2672-2678.
Boiteux et al., "The Human OGG1 Gene: Structure, Functions, and Its Implication in the Process of Carcinogenesis", *Archives of Biochemistry and Biophysics*, May 1, 2000, 377(1):1-8.
Fearnhead et al., "The ABC of APC", *Human Molecular Genetics*, 2001, 10(7):721-733.
Gu et al., "Differential DNA recognition and glycosylase activity of the native human MutY homolog (hMYH) and recombinant hMYH expressed in bacteria", *Nucleic Acids Research*, 2001, 29(12):2666-2674.
Jones et al., "Biallelic germline mutations in MYH predispose to multiple colorectal adenoma and somatic G:C→ T: A mutations", *Human Molecular Genetics*, Nov. 1, 2002, 11(23):2961-2967.
Nakabeppu, Yusaku, "Molecular genetics and structural biology of human MutT homolog, MTH1", *Mutation Research*, 2001, 477:59-70.
Ohtsubo et al., "Identification of human MutY homolog (hMYH) as a repair enzyme for 2-hydroxyadenine in DNA and detection of multiple forms of hMYH located in nuclei and mitochondria", *Nucleic Acids Research*, 2000, 28(6):1355-1364.
Shinmura et al., "Infrequent Mutations of the hOGG1 Gene, That Is Involved in the Excision of 8-Hydroxyguanine in Damaged DNA, in Human Gastric Cancer", *Jpn. J. Cancer Research*, Aug. 1998, 89:825-828.
Shinmura et al., "Somatic mutations and single nucleotide polymorphisms of base excision repair genes involved in the repair of 8-hydroxyguanine in damaged DNA", *Cancer Letters*, 2001, 166:65-69.
Slupska et al., "Cloning and Sequencing a Human Homolog (hMYH) of the *Escherichia coli* mutY Gene Whose Function Is Required for the Repair of Oxidative DNA Damage", *Journal of Bacteriology*, Jul. 1996, 178(13):3885-3892.
Sugimura et al., "hOGG1 Ser326Cys Polymorphism and Lung Cancer Susceptibility", *Cancer Epidemiology, Biomarkers & Prevention*, Aug. 1999, 8:669-674.
Tsuzuki et al., "Analysis of MTH1 gene function in mice with targeted mutagenesis", *Mutation Research*, 2001, 477:71-78.
Wikman et al., "hOGG1 Polymorphism and Loss of Heterozygosity (LOH): Significance for Lung Cancer Susceptibility in a Caucasian Population", *Int. J. Cancer*, 2000, 88:932-937.

* cited by examiner

*Primary Examiner*—Christopher M. Babic
(74) *Attorney, Agent, or Firm*—Jay Z. Zhang; Myriad Genetics IP Department

(57) ABSTRACT

Variants in MYH gene are disclosed which can result in abnormal synthesis of MYH proteins and alteration of MYH activities. The invention provides methods for detecting the newly discovered genetic variants. Use of MYH genetic variants as biomarkers in diagnosing cancer and detecting a predisposition to cancer are also disclosed herein.

14 Claims, No Drawings

SEQUENCE LISTING

<160> NUMBER OF SEQ ID NOS: 2

<210> SEQ ID NO 1
<211> LENGTH: 1869
<212> TYPE: DNA
<213> ORGANISM: Homo sapiens

<400> SEQUENCE: 1

```
tctcctcgtg gctagttcag gcggaaggag cagtcctctg aagcttgagg agcctctaga       60
actatgagcc cgaggccttc ccctctccca gagcgcagag gctttgaagg ctacctctgg      120
gaagccgctc accgtcggaa gctgcgggag ctgaaactgc gccatcgtca ctgtcggcgg      180
ccatgacacc gctcgtctcc cgcctgagtc gtctgtgggc catcatgagg aagccacgag      240
cagccgtggg aagtggtcac aggaagcagg cagccagcca ggaagggagg cagaagcatg      300
ctaagaacaa cagtcaggcc aagccttctg cctgtgatgg cctggccagg cagccggaag      360
aggtggtatt gcaggcctct gtctcctcat accatctatt cagagacgta gctgaagtca      420
cagccttccg agggagcctg ctaagctggt acgaccaaga gaaacgggac ctaccatgga      480
gaagacgggc agaagatgag atggacctgg acaggcgggc atatgctgtg tgggtctcag      540
aggtcatgct gcagcagacc caggttgcca ctgtgatcaa ctactatacc ggatggatgc      600
agaagtggcc tacactgcag gacctggcca gtgcttccct ggaggaggtg aatcaactct      660
gggctggcct gggctactat tctcgtggcc ggcggctgca ggagggagct cggaaggtgg      720
tagaggagct aggggggccac atgccacgta cagcagagac cctgcagcag ctcctgcctg      780
gcgtggggcg ctacacagct ggggccattg cctctatcgc cttttggccag caaccggtg      840
tggtggatgg caacgtagca cgggtgctgt gccgtgtccg agccattggt gctgatccca      900
gcagcaccct tgtttcccag cagctctggg gtctagccca gcagctggtg acccagccc      960
ggccaggaga tttcaaccaa gcagccatgg agctaggggc cacagtgtgt accccacagc     1020
gcccactgtg cagccagtgc cctgtggaga gcctgtgccg ggcacgccag agagtggagc     1080
aggaacagct cttagcctca gggagcctgt cgggcagtcc tgacgtggag gagtgtgctc     1140
ccaacactgg acagtgccac ctgtgcctgc ctccctcgga gccctgggac cagaccctgg     1200
gagtggtcaa cttccccaga aaggccagcc gcaagcccc cagggaggag agctctgcca     1260
cctgtgttct ggaacagcct ggggcccttg gggcccaaat tctgctggtg cagaggccca     1320
actcaggtct gctggcagga ctgtgggagt cccgtccgt gacctgggag ccctcagagc     1380
agcttcagcg caaggccctg ctgcaggaac tacagcgttg ggctgggccc ctcccagcca     1440
cgcacctccg gcaccttggg gaggttgtcc acaccttctc tcacatcaag ctgacatatc     1500
aagtatatgg gctggccttg gaagggcaga ccccagtgac caccgtacca ccaggtgctc     1560
gctggctgac gcaggaggaa tttcacaccg cagctgtttc caccgccatg aaaaaggttt     1620
tccgtgtgta tcagggccaa cagccaggga cctgtatggg ttccaaaagg tcccaggtgt     1680
cctctccgtg cagtcggaaa aagccccgca tgggccagca agtcctggat aatttctttc     1740
ggtctcacat ctccactgat gcacacagcc tcaacagtgc agcccagtga cacctctgaa     1800
agcccccatt ccctgagaat cctgttgtta gtaaagtgct tatttttgta gttaaaaaaa     1860
aaaaaaaaa                                                              1869
```

<210> SEQ ID NO 2
<211> LENGTH: 535

```
<212> TYPE: PRT
<213> ORGANISM: Homo sapiens

<400> SEQUENCE: 2

Met Thr Pro Leu Val Ser Arg Leu Ser Arg Leu Trp Ala Ile Met Arg
1               5                  10                  15

Lys Pro Arg Ala Ala Val Gly Ser Gly His Arg Lys Gln Ala Ala Ser
            20                  25                  30

Gln Glu Gly Arg Gln Lys His Ala Lys Asn Asn Ser Gln Ala Lys Pro
        35                  40                  45

Ser Ala Cys Asp Gly Leu Ala Arg Gln Pro Glu Glu Val Val Leu Gln
    50                  55                  60

Ala Ser Val Ser Ser Tyr His Leu Phe Arg Asp Val Ala Glu Val Thr
65                  70                  75                  80

Ala Phe Arg Gly Ser Leu Leu Ser Trp Tyr Asp Gln Glu Lys Arg Asp
                85                  90                  95

Leu Pro Trp Arg Arg Arg Ala Glu Asp Glu Met Asp Leu Asp Arg Arg
            100                 105                 110

Ala Tyr Ala Val Trp Val Ser Glu Val Met Leu Gln Gln Thr Gln Val
        115                 120                 125

Ala Thr Val Ile Asn Tyr Tyr Thr Gly Trp Met Gln Lys Trp Pro Thr
    130                 135                 140

Leu Gln Asp Leu Ala Ser Ala Ser Leu Glu Glu Val Asn Gln Leu Trp
145                 150                 155                 160

Ala Gly Leu Gly Tyr Tyr Ser Arg Gly Arg Arg Leu Gln Glu Gly Ala
                165                 170                 175

Arg Lys Val Val Glu Glu Leu Gly Gly His Met Pro Arg Thr Ala Glu
            180                 185                 190

Thr Leu Gln Gln Leu Leu Pro Gly Val Gly Arg Tyr Thr Ala Gly Ala
        195                 200                 205

Ile Ala Ser Ile Ala Phe Gly Gln Ala Thr Gly Val Val Asp Gly Asn
    210                 215                 220

Val Ala Arg Val Leu Cys Arg Val Arg Ala Ile Gly Ala Asp Pro Ser
225                 230                 235                 240

Ser Thr Leu Val Ser Gln Gln Leu Trp Gly Leu Ala Gln Gln Leu Val
                245                 250                 255

Asp Pro Ala Arg Pro Gly Asp Phe Asn Gln Ala Ala Met Glu Leu Gly
            260                 265                 270

Ala Thr Val Cys Thr Pro Gln Arg Pro Leu Cys Ser Gln Cys Pro Val
        275                 280                 285

Glu Ser Leu Cys Arg Ala Arg Gln Arg Val Glu Gln Glu Gln Leu Leu
    290                 295                 300

Ala Ser Gly Ser Leu Ser Gly Ser Pro Asp Val Glu Glu Cys Ala Pro
305                 310                 315                 320

Asn Thr Gly Gln Cys His Leu Cys Leu Pro Pro Ser Glu Pro Trp Asp
                325                 330                 335

Gln Thr Leu Gly Val Val Asn Phe Pro Arg Lys Ala Ser Arg Lys Pro
            340                 345                 350

Pro Arg Glu Glu Ser Ser Ala Thr Cys Val Leu Glu Gln Pro Gly Ala
        355                 360                 365

Leu Gly Ala Gln Ile Leu Leu Val Gln Arg Pro Asn Ser Gly Leu Leu
    370                 375                 380

Ala Gly Leu Trp Glu Phe Pro Ser Val Thr Trp Glu Pro Ser Glu Gln
385                 390                 395                 400
```

```
Leu Gln Arg Lys Ala Leu Leu Gln Glu Leu Gln Arg Trp Ala Gly Pro
            405                 410                 415

Leu Pro Ala Thr His Leu Arg His Leu Gly Glu Val Val His Thr Phe
            420                 425                 430

Ser His Ile Lys Leu Thr Tyr Gln Val Tyr Gly Leu Ala Leu Glu Gly
            435                 440                 445

Gln Thr Pro Val Thr Thr Val Pro Pro Gly Ala Arg Trp Leu Thr Gln
        450                 455                 460

Glu Glu Phe His Thr Ala Ala Val Ser Thr Ala Met Lys Lys Val Phe
465                 470                 475                 480

Arg Val Tyr Gln Gly Gln Gln Pro Gly Thr Cys Met Gly Ser Lys Arg
                485                 490                 495

Ser Gln Val Ser Ser Pro Cys Ser Arg Lys Lys Pro Arg Met Gly Gln
            500                 505                 510

Gln Val Leu Asp Asn Phe Phe Arg Ser His Ile Ser Thr Asp Ala His
            515                 520                 525

Ser Leu Asn Ser Ala Ala Gln
        530             535
```

US 7,670,776 B1

MYH GENE VARIANTS AND USE THEREOF

CROSS-REFERENCE TO RELATED APPLICATIONS

This application claim is a continuation-in-part of U.S. application Ser. No. 11/187,670, now U.S. Pat. No. 7,563,571 B1, filed Jul. 22, 2005 (which claims the benefit, under 35 U.S.C. §119(e), of U.S. Provisional Application Ser. No. 60/673,441, filed on Apr. 21, 2005, U.S. Provisional Application Ser. No. 60/621,298, filed on Oct. 22, 2004, and U.S. Provisional Application Ser. No. 60/590,319, filed on Jul. 22, 2004) and also claims the benefit under 35 U.S.C. § 119(e) of U.S. Provisional Application Ser. No. 60/832,387, filed on Jul. 21, 2006, each of which are incorporated herein by reference in their entireties.

SEQUENCE LISTING

A formal Sequence Listing submitted electronically as a text file has replaced the informal Sequence Listing. This text file, which was named "3006-01-3X 2007-09-17 SEQ LIST (TXT FILE) BGJ.ST25.txt", was created on Sep. 17, 2007, and is 7,632 bytes in size. Its contents are incorporated by reference herein in their entirety.

FIELD OF THE INVENTION

This invention generally relates to pharmacogenetics, particularly to the identification of genetic variants that are associated with gene expression, and methods of using the identified variants.

BRIEF DESCRIPTION OF THE SEQUENCE LISTING

SEQ ID NO: 1 contains the human MYH cDNA sequence.

SEQ ID NO:2 contains the human MYH protein sequence encoded by the nucleotide sequence of SEQ ID NO: 1.

BACKGROUND OF THE INVENTION

The human MYH gene ("MYH") encodes a protein involved in the DNA base excision repair pathway. It is the human homolog of the E. coli DNA repair gene mutY (mutY homolog: MYH). MYH encodes a DNA glycosylase involved in excising adenines misincorporated opposite 8-oxo-7,8-dihydro-2'-deoxyguanosine caused by the oxidative damage of guanine. If the defect is not repaired, G:C basepairs are mutated by transversion to T:A basepairs during DNA replication. The DNA sequence of the human MYH gene was described by Slupska et al. (J. Bacteriol. 178:3885-92 (1996)). The MYH gene has 16 exons, encodes a 535 amino acid protein, and is located on the short arm of chromosome 1, between p32.1 and p34.3.

Recently, MYH genetic variants were implicated in susceptibility to colorectal tumors in humans. Al-Tassan et al. (Nat Genet., 30:227-32 (2002)) identified a family with individuals having multiple colorectal adenomas and carcinoma. Interestingly, this family lacked inherited mutations in the APC gene (Adenomatous polyposis coli), a major colorectal cancer predisposition gene. Inherited mutations in the APC gene are known to cause familial adenomatous polyposis (FAP), an autosomal dominant disorder characterized by hundred to thousands of colorectal adenomas, some of which progress to cancer.

Analysis of tumor DNA from members of the family showed overrepresentation of mutations in the APC gene that were G:C→T:A transversions, suggesting a problem with the DNA base excision repair pathway. Subsequent analysis of the MYH gene revealed 2 missense variants. Biochemical analyses of the variants were examined in the E. coli enzyme since the human enzyme is intractable. The biochemical analysis showed that the glycosylase activity was significantly reduced for the mutants. Thus, Al-Tassan et al. linked inherited variants in MYH to the pattern of somatic APC mutation in this family and implicated defective base excision repair in predisposition to tumors in humans.

Attenuated FAP (AFAP) is associated with less adenomas (5-100) and can be caused by inherited mutations in several regions of the APC gene. Sampson et al. (Lancet, 362:39-41 (2003)) found that a significant proportion (23%) of patients from 111 families having FAP and AFAP-like presentations had biallelic mutations in MYH.

Hereditary non-polyopsis colorectal cancer (HNPPC) is another cancer that is characterized by a family history of early onset colorectal cancer in the absence of florid polyposis (Peltomaki Hum. Mol. Gen., 10:735-740 (2001)). HNPCC is associated with deleterious mutations in the genes encoding the mismatch repair pathway enzymes, particularly in the MLH1 and MSH2 genes.

As MYH plays an important role in DNA base excision repair, mutations that result in alterations of MYH protein structure and/or biological activity can lead to an overall increase of mutation rate and are associated with predisposition to cancers. Thus, it is desirable to identify additional deleterious mutations in the MYH gene, which may serve as potential diagnostic markers and therapeutic targets.

SUMMARY OF THE INVENTION

The present invention is based on the discovery of a number of genetic mutations in the MYH gene. The nucleotide and amino acid variants are summarized below in the Detailed Description of the Invention. The variants can be deleterious and cause significant alterations in the structure, biochemical activity, and/or expression level of the human MYH protein. Thus, the nucleotide variants can be useful in genetic testing as markers for the prediction of predisposition to cancers, especially colorectal cancer, and in therapeutic applications for treating cancers.

Accordingly, in a first aspect of the present invention, an isolated human MYH nucleic acid is provided containing at least one of the newly discovered genetic polymorphic variants as summarized in Table 1 below. The present invention also encompasses an isolated oligonucleotide having a contiguous span of at least 18, preferably from 18 to 50 nucleotides of the sequence of a human MYH gene, wherein the contiguous span encompasses and contains a nucleotide variant selected from those in Table 1.

DNA microchips are also provided comprising an isolated MYH gene or an isolated oligonucleotide according to the present invention. In accordance with another aspect of the invention, an isolated MYH protein or a fragment thereof is provided having an amino acid variant selected from those in Table 1.

In accordance with another aspect of the invention, a deleterious MYH mutant protein or gene is provided herein.

The present invention also provides an isolated antibody specifically immunoreactive with a MYH protein variant of the present invention.

In accordance with yet another aspect of the present invention, a method is provided for genotyping the MYH gene of an individual by determining whether the individual has a genetic variant or an amino acid variant provided in accordance with the present invention. In addition, the present invention also provides a method for predicting in an individual a predisposition to cancer (e.g., colorectal cancer). The method comprises the step of detecting in the individual the presence or absence of a genetic variant or amino acid variant provided according to the present invention.

In accordance with yet another aspect of the invention, a detection kit is also provided for detecting, in an individual, an elevated risk of cancer. In a specific embodiment, the kit is used in determining a predisposition to cancer such as colorectal cancer. The kit may include, in a carrier or confined compartment, any nucleic acid probes or primers, or antibodies useful for detecting the nucleotide variants or amino acid variants of the present invention as described above. The kit can also include other reagents such as DNA polymerase, buffers, nucleotides and others that can be used in the method of detecting the variants according to this invention. In addition, the kit preferably also contains instructions for using the kit.

The foregoing and other advantages and features of the invention, and the manner in which the same are accomplished, will become more readily apparent upon consideration of the following detailed description of the invention taken in conjunction with the accompanying examples and drawings, which illustrate preferred and exemplary embodiments.

DETAILED DESCRIPTION OF THE INVENTION

1. Definitions

The terms "genetic variant" and "nucleotide variant" are used herein interchangeably to refer to changes or alterations to the reference human MYH gene or cDNA sequence at a particular locus, including, but not limited to, nucleotide base deletions, insertions, inversions, and substitutions in the coding and noncoding regions. Deletions may be of a single nucleotide base, a portion or a region of the nucleotide sequence of the gene, or of the entire gene sequence. Insertions may be of one or more nucleotide bases. The "genetic variant" or "nucleotide variants" may occur in transcriptional regulatory regions, untranslated regions of mRNA, exons, introns, or exon/intron junctions. The "genetic variant" or "nucleotide variants" may or may not result in stop codons, frame shifts, deletions of amino acids, altered gene transcript splice forms or altered amino acid sequence.

The term "allele" or "gene allele" is used herein to refer generally to a naturally occurring gene having a reference sequence or a gene containing a specific nucleotide variant.

As used herein, "haplotype" is a combination of genetic (nucleotide) variants in a region of an mRNA or a genomic DNA on a chromosome found in an individual. Thus, a haplotype includes a number of genetically linked polymorphic variants which are typically inherited together as a unit.

As used herein, the term "amino acid variant" is used to refer to an amino acid change to a reference human MYH protein sequence resulting from "genetic variants" or "nucleotide variants" to the reference human gene encoding the reference MYH protein. The term "amino acid variant" is intended to encompass not only single amino acid substitutions, but also amino acid deletions, insertions, and other significant changes of amino acid sequence in the reference MYH protein.

The term "genotype" as used herein means the nucleotide characters at a particular nucleotide variant marker (or locus) in either one allele or both alleles of a gene (or a particular chromosome region). With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, that is, the nucleotide(s) at a particular gene locus. Genotyping can also be done by determining the amino acid variant at a particular position of a protein which can be used to deduce the corresponding nucleotide variant(s).

As used herein, the term "MYH nucleic acid" means a nucleic acid molecule the nucleotide sequence of which is uniquely found in an MYH gene. That is, a "MYH nucleic acid" is either an MYH genomic DNA or mRNA/cDNA, having a naturally existing nucleotide sequence encoding a naturally existing MYH protein (wild-type or mutant form). The sequence of an example of a naturally existing MYH nucleic acid is found in GenBank Accession No. U63329 (PRI 28-JUL-1996) (see SEQ ID NO:1).

As used herein, the term "MYH protein" means a polypeptide molecule the amino acid sequence of which is found uniquely in an MYH protein. That is, "MYH protein" is a naturally existing MYH protein (wild-type or mutant form). The sequence of a wild-type form of a MYH protein is found in GenBank Accession No. U63329 (PRI 28-JUL-1996) (see SEQ ID NO:2).

The term "locus" refers to a specific position or site in a gene sequence or protein. Thus, there may be one or more contiguous nucleotides in a particular gene locus, or one or more amino acids at a particular locus in a polypeptide. Moreover, "locus" may also be used to refer to a particular position in a gene where one or more nucleotides have been deleted, inserted, or inverted.

As used herein, the terms "polypeptide," "protein," and "peptide" are used interchangeably to refer to an amino acid chain in which the amino acid residues are linked by covalent peptide bonds. The amino acid chain can be of any length of at least two amino acids, including full-length proteins. Unless otherwise specified, the terms "polypeptide," "protein," and "peptide" also encompass various modified forms thereof, including but not limited to glycosylated forms, phosphorylated forms, etc.

The terms "primer", "probe," and "oligonucleotide" are used herein interchangeably to refer to a relatively short nucleic acid fragment or sequence. They can be DNA, RNA, or a hybrid thereof, or chemically modified analog or derivatives thereof. Typically, they are single-stranded. However, they can also be double-stranded having two complementing strands which can be separated apart by denaturation. Normally, they have a length of from about 8 nucleotides to about 200 nucleotides, preferably from about 12 nucleotides to about 100 nucleotides, and more preferably about 18 to about 50 nucleotides. They can be labeled with detectable markers or modified in any conventional manners for various molecular biological applications.

The term "isolated" when used in reference to nucleic acids (e.g., genomic DNAs, cDNAs, mRNAs, or fragments thereof) is intended to mean that a nucleic acid molecule is present in a form that is substantially separated from other naturally occurring nucleic acids that are normally associated with the molecule. Specifically, since a naturally existing chromosome (or a viral equivalent thereof) includes a long nucleic acid sequence, an "isolated nucleic acid" as used herein means a nucleic acid molecule having only a portion of the nucleic acid sequence in the chromosome but not one or more other portions present on the same chromosome. More specifically, an "isolated nucleic acid" typically includes no more than 25 kb naturally occurring nucleic acid sequences which immediately flank the nucleic acid in the naturally existing chromosome (or a viral equivalent thereof). However, it is noted that an "isolated nucleic acid" as used herein is distinct from a clone in a conventional library such as genomic DNA library and cDNA library in that the clone in a library is still in admixture with almost all the other nucleic acids of a chromosome or cell. Thus, an "isolated nucleic acid" as used herein also should be substantially separated from other naturally occurring nucleic acids that are on a different chromosome of the same organism. Specifically, an "isolated nucleic acid" means a composition in which the specified nucleic acid molecule is significantly enriched so as to constitute at least 10% of the total nucleic acids in the composition.

An "isolated nucleic acid" can be a hybrid nucleic acid having the specified nucleic acid molecule covalently linked to one or more nucleic acid molecules that are not the nucleic acids naturally flanking the specified nucleic acid. For example, an isolated nucleic acid can be in a vector. In addition, the specified nucleic acid may have a nucleotide sequence that is identical to a naturally occurring nucleic acid or a modified form or mutein thereof having one or more mutations such as nucleotide substitution, deletion/insertion, inversion, and the like.

An isolated nucleic acid can be prepared from a recombinant host cell (in which the nucleic acids have been recombinantly amplified and/or expressed), or can be a chemically synthesized nucleic acid having a naturally occurring nucleotide sequence or an artificially modified form thereof.

The term "isolated polypeptide" as used herein is defined as a polypeptide molecule that is present in a form other than that found in nature. Thus, an isolated polypeptide can be a non-naturally occurring polypeptide. For example, an "isolated polypeptide" can be a "hybrid polypeptide." An "isolated polypeptide" can also be a polypeptide derived from a naturally occurring polypeptide by additions or deletions or substitutions of amino acids. An isolated polypeptide can also be a "purified polypeptide" which is used herein to mean a composition or preparation in which the specified polypeptide molecule is significantly enriched so as to constitute at least 10% of the total protein content in the composition. A "purified polypeptide" can be obtained from natural or recombinant host cells by standard purification techniques, or by chemically synthesis, as will be apparent to skilled artisans.

The terms "hybrid protein," "hybrid polypeptide," "hybrid peptide," "fusion protein," "fusion polypeptide," and "fusion peptide" are used herein interchangeably to mean a non-naturally occurring polypeptide or isolated polypeptide having a specified polypeptide molecule covalently linked to one or more other polypeptide molecules that do not link to the specified polypeptide in nature. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

The term "high stringency hybridization conditions," when used in connection with nucleic acid hybridization, means hybridization conducted overnight at 42 degrees C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 0.1×SSC at about 65° C. The term "moderate stringent hybridization conditions," when used in connection with nucleic acid hybridization, means hybridization conducted overnight at 37 degrees C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 1×SSC at about 50° C. It is noted that many other hybridization methods, solutions and temperatures can be used to achieve comparable stringent hybridization conditions as will be apparent to skilled artisans.

For the purpose of comparing two different nucleic acid or polypeptide sequences, one sequence (test sequence) may be described to be a specific "percentage identical to" another sequence (comparison sequence) in the present disclosure. In this respect, the percentage identity is determined by the algorithm of Karlin and Altschul, *Proc. Natl. Acad. Sci. USA*, 90:5873-5877 (1993), which is incorporated into various BLAST programs. Specifically, the percentage identity is determined by the "BLAST 2 Sequences" tool, which is available at NCBI's website. See Tatusova and Madden, *FEMS Microbiol. Lett.*, 174(2):247-250 (1999). For pairwise DNA-DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter). Percent identity of two sequences is calculated by aligning a test sequence with a comparison sequence using BLAST 2.1.2., determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. When BLAST 2.1.2 is used to compare two sequences, it aligns the sequences and yields the percent identity over defined, aligned regions. If the two sequences are aligned across their entire length, the percent identity yielded by the BLAST 2.1.1 is the percent identity of the two sequences. If BLAST 2.1.2 does not align the two sequences over their entire length, then the number of identical amino acids or nucleotides in the unaligned regions of the test sequence and comparison sequence is considered to be zero and the percent identity is calculated by adding the number of identical amino acids or nucleotides in the aligned regions and dividing that number by the length of the comparison sequence.

The term "reference sequence" refers to a polynucleotide or polypeptide sequence known in the art, including those disclosed in publicly accessible databases, e.g., GenBank, or a newly identified gene sequence, used simply as a reference with respect to the nucleotide variants provided in the present invention. The nucleotide or amino acid sequence in a reference sequence is contrasted to the alleles disclosed in the present invention having newly discovered nucleotide or amino acid variants. In the instant disclosure, for genomic DNA, the sequence in GenBank Accession No. NT_032977 (PRI 19-AUG-2004) is used as a reference sequence, while the nucleotide and amino acid sequences in GenBank Accession No. U63329 (PRI 28-JUL-1996) (see SEQ ID NOs: 1 and 2) are used as the reference sequences for MYH cDNA and proteins, respectively.

2. Nucleotide and Amino Acid Variants

Thus, in accordance with the present invention, genetic variants have been discovered in the MYH gene. The identified polymorphisms are summarized in Table 1 below.

Thus, in accordance with the present invention, a number of genetic variants have been discovered in genetic tests that analyze the MYH gene in different individuals that have colorectal cancer. The MYH variants include those detected in APC negative patient samples (patients having FAP that did not have a deleterious mutation in the APC gene) and those detected in HNPCC negative patient samples (patients having HNPCC that did not have a deleterious mutation in MLH1 and MSH2). The variants detected in the APC negative patients include truncating mutations E182X (544G→T) and Q300X (898C→T), deletion mutations IVS13+25 del30, putative splice mutations IVS12-2 A→G, missense variants D147H (439G→C), R168L (503G→C), P391L (1172C→T), A405T (1213G→A), A475T (1423G→A), R231H (692G→A) and translationally silent variants D75D (225C→T). The variants discovered in HNPCC negative patients include missense variants M15V (43A→G), Q324R (971A→G), F344Y (1031T→A), P345T (1033C→A), and L406M (1216C→A). Other nucleotide variants discovered include 500C→T (S167F), 423G→A (silent), and 1506G→A (silent), 283C→T (R95W) and NVS6-4 A→G. An additional nucleotide variant, 691C→T (or in reference to SEQ ID NO: 1 873 C→T), was discovered that corresponds to a R231C amino acid variant in the MYH protein.

The variant positions are assigned by aligning the variant allele sequence to the above-identified cDNA and/or genomic reference sequences, with the starting nucleotide (nucleotide+1) being the A in the start codon ATG in the reference cDNA sequence. The positions in an intron or intervening sequence (IVS) are assigned relative to the exon immediately preceding or following the intron. Thus, for example, IVS13+25 del30 means a deletion of 30 nucleotides (in contrast to the presence of the 30 nucleotides in the reference sequence) at the 25$^{th}$ nucleotide position counting from the first nucleotide of the intron (or IVS) 13 immediately following the exon immediately preceding the intron, i.e., exon 13. IVS12-2A→G means a nucleotide polymorphism of guanine (in contrast to adenine in the reference sequence) at the −2 nucleotide position counting in the downstream to upstream direction from the intronic nucleotide immediately preceding exon 12. In other words, positive numbers start from the G of the donor site invariant GT, while negative numbers start from the G of the acceptor site invariant AG.

The amino acid substitutions caused by the nucleotide variants are also identified according to conventional practice. For example, R168L means the amino acid variant at position 168 is leucine in contrast to arginine in the reference sequence. The standard one letter code for amino acids and nucleotides is used throughout, X indicates a stop codon.

TABLE 1

Genetic Variants in the MYH Gene

| SNP Position | Amino Acid Variant |
|---|---|
| 43A→G | M15V |
| 225C→T | D75D |
| 283C→T | R95W |
| 423G→A | K141K |
| 439G→C | D147H |
| 500C→T | S167F |
| 503G→T | R168L |
| 544G→T | E182X |
| 691C→T | R231C |
| 692G→A | R231H |
| 898C→T | Q300X |
| 971A→G | Q324R |
| 1031T→A | F344Y |
| 1033C→A | P345T |
| 1172C→T | P391L |
| 1213G→A | A405T |
| 1216C→A | L406M |
| 1423G→A | A475T |
| 1506G→A | P502P |
| IVS6-4 A→G | intronic |
| IVS12-2 A→G | intronic |
| IVS13 + 25del30 | intronic |

3. Isolated Nucleic Acids

Accordingly, the present invention provides an isolated MYH nucleic acid containing at least one of the newly discovered nucleotide variants as summarized in Table 1, or one or more nucleotide variants that will result in the amino acid variants provided in Table 1, e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A, 692G→A, IVS6-4 A→G, IVS12-2A→G, and IVS13+25del30. The term "MYH nucleic acid" is as defined above and means a naturally existing nucleic acid coding for a wild-type or variant or mutant MYH. The term "MYH nucleic acid" is inclusive and may be in the form of either double-stranded or single-stranded nucleic acids, and a single strand can be either of the two complementing strands. The isolated MYH nucleic acid can be naturally existing genomic DNA, mRNA or cDNA. In one embodiment, the isolated MYH nucleic acid has a nucleotide sequence according to SEQ ID NO: 1 but containing one or more exonic nucleotide variants of Table 1 (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A and 692G→A), or the complement thereof.

In another embodiment, the isolated MYH nucleic acid has a nucleotide sequence that is at least 95%, preferably at least 97% and more preferably at least 99% identical to SEQ ID NO: 1 but contains one or more exonic nucleotide variants of Table 1 (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A and 692G→A), or one or more nucleotide variants that will result in one or more amino acid variants of Table 1, or the complement thereof.

In yet another embodiment, the isolated MYH nucleic acid has a nucleotide sequence encoding MYH protein having an amino acid sequence according to SEQ ID NO:2 but contains one or more amino acid variants of Table 1 (e.g., 43A→G, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T and 692G→A). Isolated MYH nucleic acids having a nucleotide sequence that is the complement of the sequence are also encompassed by the present invention.

In yet another embodiment, the isolated MYH nucleic acid has a nucleotide sequence encoding a MYH protein having an amino acid sequence that is at least 95%, preferably at least 97% and more preferably at least 99% identical to SEQ ID NO:2 but contains one or more amino acid variants of Table 1 (e.g., 43A→G, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T and 692G→A), or the complement thereof.

The present invention also provides an isolated nucleic acid, naturally occurring or artificial, having a nucleotide sequence that is at least 95%, preferably at least 97% and more preferably at least 99% identical to SEQ ID NO: 1 except for containing one or more nucleotide variants of Table 1 (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A and 692G→A), or the complement thereof.

In another embodiment, the present invention provides an isolated nucleic acid, naturally occurring or artificial, having a nucleotide sequence encoding a MYH protein having an amino acid sequence according to SEQ ID NO:2 but containing one or more amino acid variants of Table 1 (e.g., 43A→G, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T and 692G→A). Isolated nucleic acids having a nucleotide sequence that is the complement of the sequence are also encompassed by the present invention.

In addition, isolated nucleic acids are also provided which have a nucleotide sequence encoding a protein having an amino acid sequence that is at least 95%, preferably at least 97% and more preferably at least 99% identical to SEQ ID NO:2 but containing one or more amino acid variants of Table 1 (e.g., 43A→G, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T and 692G→A), or the complement thereof.

Also encompassed are isolated MYH nucleic acids obtainable by:

(a) providing a human genomic library;

(b) screening the genomic library using a probe having a nucleotide sequence according to SEQ ID NO: 1; and (c) producing a genomic DNA comprising a contiguous span of at least 30 nucleotides of any one of SEQ ID NO: 1, wherein the genomic DNA thus produced contains one or more of the polymorphisms of the present invention in Table 1, such as 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A, 692G→A, IVS6-4 A→G, IVS12-2A→G and IVS13+25del30.

The present invention also includes isolated MYH nucleic acids obtainable by:

(i) providing a cDNA library using human mRNA from a human tissue, e.g., blood;

(ii) screening the cDNA library using a probe having a nucleotide sequence according to SEQ ID NO: 1; and (iii) producing a cDNA DNA comprising a contiguous span of at least 30 nucleotides of SEQ ID NOs:1, wherein the cDNA thus produced contains one or more of the SNPs of the present invention in Table 1, such as 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A and 692G→A.

The present invention also encompasses an isolated nucleic acid comprising the nucleotide sequence of a region of a MYH genomic DNA or cDNA or mRNA, wherein the region contains one or more nucleotide variants as provided in Table 1 above (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A, 692G→A, IVS6-4 A→G, IVS12-2A→G and IVS13+25del30), or one or more nucleotide variants that will give rise to one or more amino acid variants of Table 1, or the complement thereof. Such regions can be isolated and analyzed to efficiently detect the nucleotide variants of the present invention. Also, such regions can also be isolated and used as probes or primers in detection of the nucleotide variants of the present invention and other uses as will be clear from the descriptions below.

Thus, in one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of a MYH nucleic acid, the contiguous span containing one or more nucleotide variants of Table 1 (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A, 692G→A, IVS6-4 A→G, IVS12-2A→G and IVS13+25del30), or the complement thereof. In specific embodiments, the isolated nucleic acid are oligonucleotides having a contiguous span of from about 17, 18, 19, 20, 21, 22, 23 or 25 to about 30, 40 or 50, preferably from about 21 to about 30 nucleotide residues, of any MYH nucleic acid, said contiguous span containing one or more nucleotide variants of Table 1 (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A, 692G→A, IVS6-4 A→G, IVS12-2A→G and IVS13+25del30).

In one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of any one of SEQ ID NO: 1, containing one or more nucleotide variants of Table 1 (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A, 692G→A, IVS6-4 A→G, IVS12-2A→G and IVS13+25del30), or the complement thereof. In specific embodiments, the isolated nucleic acid comprises a nucleotide sequence according to SEQ ID NO: 1. In preferred embodiments, the isolated nucleic acid are oligonucleotides having a contiguous span of from about 17, 18, 19, 20, 21, 22, 23 or 25 to about 30, 40 or 50, preferably from about 21 to about 30 nucleotide residues, of any one of SEQ ID NO: 1 and containing one or more nucleotide variants of Table 1 (e.g., 43A→G, 225C→T, 283C→T, 544G→T, 898C→T, 439G→C, 503G→C, 691C→T, 1172C→T, 1213G→A, 1423G→A, 971A→G, 1031T→A, 1033C→A, 1216C→A, 500C→T, 423G→A, 1506G→A, 692G→A, IVS6-4 A→G, IVS12-2A→G and IVS13+25del30). The complements of the isolated nucleic acids are also encompassed by the present invention.

In preferred embodiments, an isolated oligonucleotide of the present invention is specific to a MYH allele ("allele-specific") containing one or more nucleotide variants as disclosed in the present invention. That is, the isolated oligonucleotide is capable of selectively hybridizing, under high stringency conditions generally recognized in the art, to a MYH genomic or cDNA or mRNA containing one or more nucleotide variants as disclosed in the present invention, but not to a MYH gene having a reference sequence of SEQ ID NO: 1. Such oligonucleotides will be useful in a hybridization-based method for detecting the nucleotide variants of the present invention as described in details below. An ordinarily skilled artisan would recognize various stringent conditions which enable the oligonucleotides of the present invention to differentiate between a MYH gene having a reference sequence and a variant MYH gene of the present invention. For example, the hybridization can be conducted overnight in a solution containing 50% formamide, 5×SSC, pH7.6, 5×Denhardt's solution, 10% dextran sulfate, and 20 microgram/ml denatured, sheared salmon sperm DNA. The hybridization filters can be washed in 0.1×SSC at about 65° C. Alternatively, typical PCR conditions employed in the art with an annealing temperature of about 55° C. can also be used.

In the isolated MYH oligonucleotides containing a nucleotide variant according to the present invention, the nucleotide variant can be located in any position. In one embodiment, a nucleotide variant is at the 5' or 3' end of the oligonucleotides. In a more preferred embodiment, a MYH oligonucleotide contains only one nucleotide variant according to the present invention, which is located at the 3' end of the oligonucleotide. In another embodiment, a nucleotide variant of the present invention is located within no greater than four (4), preferably no greater than three (3), and more preferably no greater than two (2) nucleotides of the center of the oligonucleotide of the present invention. In more preferred embodiment, a nucleotide variant is located at the center or within one (1) nucleotide of the center of the oligonucleotide. For purposes of defining the location of a nucleotide variant in an oligonucleotide, the center nucleotide of an oligonucleotide with an odd number of nucleotides is considered to be the center. For an oligonucleotide with an even number of nucleotides, the bond between the two center nucleotides is considered to be the center.

In other embodiments of the present invention, isolated nucleic acids are provided which encode a contiguous span of at least 6, 7, 8, 9, 10, 11, 12, 13, 14, 15, 16 or 17 amino acids of a MYH protein wherein said contiguous span contains at least one amino acid variant in Table 1 according to the present invention.

The oligonucleotides of the present invention can have a detectable marker selected from, e.g., radioisotopes, fluorescent compounds, enzymes, or enzyme co-factors operably linked to the oligonucleotide. The oligonucleotides of the present invention can be useful in genotyping as will be apparent from the description below.

In addition, the present invention also provides DNA microchips or microarray incorporating a variant MYH genomic DNA or cDNA or mRNA or an oligonucleotide according to the present invention. The microchip will allow rapid genotyping and/or haplotyping in a large scale.

As is known in the art, in microchips, a large number of different nucleic acid probes are attached or immobilized in an array on a solid support, e.g., a silicon chip or glass slide.

Target nucleic acid sequences to be analyzed can be contacted with the immobilized oligonucleotide probes on the microchip. See Lipshutz et al., *Biotechniques,* 19:442-447 (1995); Chee et al., *Science,* 274:610-614 (1996); Kozal et al., *Nat. Med.* 2:753-759 (1996); Hacia et al., *Nat. Genet.,* 14:441-447 (1996); Saiki et al., *Proc. Natl. Acad. Sci. USA,* 86:6230-6234 (1989); Gingeras et al., *Genome Res.,* 8:435-448 (1998). The microchip technologies combined with computerized analysis tools allow large-scale high throughput screening. See, e.g., U.S. Pat. No. 5,925,525 to Fodor et al; Wilgenbus et al., *J. Mol. Med.,* 77:761-786 (1999); Graber et al., *Curr. Opin. Biotechnol.,* 9:14-18 (1998); Hacia et al., *Nat. Genet.,* 14:441-447 (1996); Shoemaker et al., *Nat. Genet.,* 14:450-456 (1996); DeRisi et al., *Nat. Genet.,* 14:457-460 (1996); Chee et al., *Nat. Genet.,* 14:610-614 (1996); Lockhart et al., *Nat. Genet.,* 14:675-680 (1996); Drobyshev et al., *Gene,* 188: 45-52 (1997).

In a preferred embodiment, a DNA microchip is provided comprising a plurality of the oligonucleotides of the present invention such that the nucleotide identity at each of the nucleotide variant sites disclosed in Table 1 can be determined in one single microarray. In a preferred embodiment, the microchip incorporates variant MYH nucleic acid or oligonucleotide of the present invention and contains at least two of the variants in Table 1, preferably at least three, more preferably at least four of the variants in Table 1.

4. MYH Protein and Peptide

The present invention also provides isolated proteins encoded by one of the isolated nucleic acids according to the present invention. In one aspect, the present invention provides an isolated MYH protein encoded by one of the novel MYH gene variants according to the present invention. Thus, for example, the present invention provides an isolated MYH protein having an amino acid sequence according to SEQ ID NO:2 but containing one or more amino acid variants selected from the group consisting of M15V, R95W, D147H, S167F, R168L, E182X, Q300X, R231H, R231c, Q324R, F344Y, P345T, P391L, A405T, L406M and A475T. In another example, the isolated MYH protein of the present invention has an amino acid sequence at least 95%, preferably 97%, more preferably 99% identical to SEQ ID NO:2 wherein the amino acid sequence contains at least one amino acid variant selected from the group consisting of M15V, R95W, D147H, S167F, R168L, E182X, Q300X, R231H, R231c, Q324R, F344Y, P345T, P391L, A405T, L406M and A475T.

In addition, the present invention also encompasses isolated peptides having a contiguous span of at least 6, 7, 8, 9, 10, 11, 12, 13, 15, 17, 19 or 21 or more amino acids of an isolated MYH protein of the present invention said contiguous span encompassing one or more amino acid variants selected from the group consisting of M15V, R95W, D147H, S167F, R168L, E182X, Q300X, R231H, R231c, Q324R, F344Y, P345T, P391L, A405T, L406M and A475T. In preferred embodiments, the isolated variant MYH peptides contain no greater than 200 or 100 amino acids, and preferably no greater than 50 amino acids. In specific embodiments, the MYH polypeptides in accordance with the present invention contain one or more of the amino acid variants identified in accordance with the present invention. The peptides can be useful in preparing antibodies specific to the mutant MYH proteins provided in accordance with the present invention.

Thus, as an example, an isolated polypeptide of the present invention can have a contiguous span of at least 6, 7, 8, 9, 10, 11, 12, 13, 14 or 15 amino acid residues of SEQ ID NO: 1 encompassing the amino acid variant M15V (amino acid residue No. 15 in SEQ ID NO:2), or a contiguous span of at least 6, 7, 8, 9, 10, 11, 12, 13, 14 or 15 amino acid residues of SEQ ID NO: 1 encompassing the amino acid variant R95W (amino acid residue No. 95 in SEQ ID NO:2), or a contiguous span of at least 6, 7, 8, 9, 10, 11, 12, 13, 14 or 15 amino acid residues of SEQ ID NO: 1 encompassing the amino acid variant D147H (amino acid residue No. 147 in SEQ ID NO:2), or a contiguous span of at least 6, 7, 8, 9, 10, 11, 12, 13, 14 or 15 amino acid residues of SEQ ID NO: 1 encompassing the amino acid variant S167F (amino acid residue No. 167 in SEQ ID NO:2), or a contiguous span of at least 6, 7, 8, 9, 10, 11, 12, 13, 14 or 15 amino acid residues of SEQ ID NO: 1 encompassing the amino acid variant R168L (amino acid residue No. 168 in SEQ ID NO:2), or a contiguous span of at least 6, 7, 8, 9, 10, 11, 12, 13, 14 or 15 amino acid residues of SEQ ID NO: 1 encompassing the amino acid variant E182X (amino acid residue No. 182 in SEQ ID NO:2), or a contiguous span of at least 6, 7, 8, 9, 10, 11, 12, 13, 14 or 15 amino acid residues of SEQ ID NO: 1 encompassing the amino acid variant Q300X (amino acid residue No. 300 in SEQ ID NO:2), or a contiguous span of at least 6, 7, 8, 9, 10, 11, 12, 13, 14 or 15 amino acid residues of SEQ ID NO: 1 encompassing the amino acid variant R231H (amino acid residue No. 231 in SEQ ID NO:2), or a contiguous span of at least 6, 7, 8, 9, 10, 11, 12, 13, 14 or 15 amino acid residues of SEQ ID NO: 1 encompassing the amino acid variant R231C (amino acid residue No. 231 in SEQ ID NO:2), or a contiguous span of at least 6, 7, 8, 9, 10, 11, 12, 13, 14 or 15 amino acid residues of SEQ ID NO: 1 encompassing the amino acid variant Q324R (amino acid residue No. 324 in SEQ ID NO:2), or a contiguous span of at least 6, 7, 8, 9, 10, 11, 12, 13, 14 or 15 amino acid residues of SEQ ID NO: 1 encompassing the amino acid variant F344Y (amino acid residue No. 344 in SEQ ID NO:2), or a contiguous span of at least 6, 7, 8, 9, 10, 11, 12, 13, 14 or 15 amino acid residues of SEQ ID NO: 1 encompassing the amino acid variant P345T (amino acid residue No. 345 in SEQ ID NO:2), or a contiguous span of at least 6, 7, 8, 9, 10, 11, 12, 13, 14 or 15 amino acid residues of SEQ ID NO:1 encompassing the amino acid variant P391L (amino acid residue No. 391 in SEQ ID NO:2), or a contiguous span of at least 6, 7, 8, 9, 10, 11, 12, 13, 14 or 15 amino acid residues of SEQ ID NO: 1 encompassing the amino acid variant A405T (amino acid residue No. 405 in SEQ ID NO:2), or a contiguous span of at least 6, 7, 8, 9, 10, 11, 12, 13, 14 or 15 amino acid residues of SEQ ID NO: 1 encompassing the amino acid variant L406M (amino acid residue No. 406 in SEQ ID NO:2), or a contiguous span of at least 6, 7, 8, 9, 10, 11, 12, 13, 14 or 15 amino acid residues of SEQ ID NO: 1 encompassing the amino acid variant A475T (amino acid residue No. 475 in SEQ ID NO:2).

As will be apparent to an ordinarily skilled artisan, the isolated nucleic acids and isolated polypeptides of the present invention can be prepared using techniques generally known in the field of molecular biology. See generally, Sambrook et al., *Molecular Cloning: A Laboratory Manual*, 2$^{nd}$ ed., Cold Spring Harbor Laboratory, Cold Spring Harbor, N.Y., 1989. The isolated MYH gene or cDNA or oligonucleotides of this invention can be operably linked to one or more other DNA fragments. For example, the isolated MYH nucleic acid (e.g., cDNA or oligonucleotides) can be ligated to another DNA such that a fusion protein can be encoded by the ligation product. The isolated MYH nucleic acid (e.g., cDNA or oligonucleotides) can also be incorporated into a DNA vector for purposes of, e.g., amplifying the nucleic acid or a portion thereof, and/or expressing a mutant MYH polypeptide or a fusion protein thereof.

Thus, the present invention also provides a vector construct containing an isolated nucleic acid of the present invention, such as a mutant MYH nucleic acid (e.g., cDNA or oligonucleotides) of the present invention. Generally, the vector construct may include a promoter operably linked to a DNA of interest (including a full-length sequence or a fragment thereof in the 5' to 3' direction or in the reverse direction for purposes of producing antisense nucleic acids), an origin of DNA replication for the replication of the vector in host cells and a replication origin for the amplification of the vector in, e.g., *E. coli*, and selection marker(s) for selecting and maintaining only those host cells harboring the vector. Additionally, the vector preferably also contains inducible elements, which function to control the expression of the isolated gene sequence. Other regulatory sequences such as transcriptional termination sequences and translation regulation sequences (e.g., Shine-Dalgarno sequence) can also be included. An epitope tag-coding sequence for detection and/or purification of the encoded polypeptide can also be incorporated into the vector construct. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vector construct can be introduced into the host cells or organisms by any techniques known in the art, e.g., by direct DNA transformation, microinjection, electroporation, viral infection, lipofection, gene gun, and the like. The vector construct can be maintained in host cells in an extrachromosomal state, i.e., as self-replicating plasmids or viruses. Alternatively, the vector construct can be integrated into chromosomes of the host cells by conventional techniques such as selection of stable cell lines or site-specific recombination. The vector construct can be designed to be suitable for expression in various host cells, including but not limited to bacteria, yeast cells, plant cells, insect cells, and mammalian and human cells. A skilled artisan will recognize that the designs of the vectors can vary with the host cell used.

5. Antibodies

The present invention also provides antibodies selectively immunoreactive with a variant MYH protein or peptide provided in accordance with the present invention and methods for making the antibodies. As used herein, the term "antibody" encompasses both monoclonal and polyclonal antibodies that fall within any antibody classes, e.g., IgG, IgM, IgA, etc. The term "antibody" also means antibody fragments including, but not limited to, Fab and F(ab')$_2$, conjugates of such fragments, and single-chain antibodies that can be made in accordance with U.S. Pat. No. 4,704,692, which is incorporated herein by reference. Specifically, the phrase "selectively immunoreactive with one or more of the newly discovered variant MYH protein variants" as used herein means that the immunoreactivity of an antibody with a protein variant of the present invention is substantially higher than that with the MYH protein heretofore known in the art such that the binding of the antibody to the protein variant of the present invention is readily distinguishable, based on the strength of the binding affinities, from the binding of the antibody to the MYH protein having a reference amino acid sequence. Preferably, the binding constant differs by a magnitude of at least 2 fold, more preferably at least 5 fold, even more preferably at least 10 fold, and most preferably at least 100 fold.

To make such an antibody, a variant MYH protein or a peptide of the present invention having a particular amino acid variant (e.g., substitution or insertion or deletion) is provided and used to immunize an animal. The variant MYH protein or peptide variant can be made by any methods known in the art, e.g., by recombinant expression or chemical synthesis. To increase the specificity of the antibody, a shorter peptide containing an amino acid variant is preferably generated and used as antigen. Techniques for immunizing animals for the purpose of making polyclonal antibodies are generally known in the art. See Harlow and Lane, *Antibodies: A Laboratory Manual*, Cold Spring Harbor Laboratory, Cold Spring Harbor, N.Y., 1988. A carrier may be necessary to increase the immunogenicity of the polypeptide. Suitable carriers known in the art include, but are not limited to, liposome, macromolecular protein or polysaccharide, or combination thereof. Preferably, the carrier has a molecular weight in the range of about 10,000 to 1,000,000. The polypeptide may also be administered along with an adjuvant, e.g., complete Freund's adjuvant.

The antibodies of the present invention preferably are monoclonal. Such monoclonal antibodies may be developed using any conventional techniques known in the art. For example, the popular hybridoma method disclosed in Kohler and Milstein, *Nature*, 256:495-497 (1975) is now a well-developed technique that can be used in the present invention. See U.S. Pat. No. 4,376,110, which is incorporated herein by reference. Essentially, B-lymphocytes producing a polyclonal antibody against a protein variant of the present invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, *Antibodies: A Laboratory Manual*, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, antibodies selectively immunoreactive with a protein or peptide variant of the present invention may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific protein may then be isolated from the library. The isolated cDNA can be introduced into a suitable host cell for the expression of the protein. Thus, recombinant techniques can be used to recombinantly produce specific native antibodies, hybrid antibodies capable of simultaneous reaction with more than one antigen, chimeric antibodies (e.g., the constant and variable regions are derived from different sources), univalent antibodies which comprise one heavy and light chain pair coupled with the Fc region of a third (heavy) chain, Fab proteins, and the like. See U.S. Pat. No. 4,816,567; European Patent Publication No. 0088994; Munro, *Nature,* 312:597 (1984); Morrison, *Science,* 229:1202 (1985); Oi et al., *BioTechniques,* 4:214 (1986); and Wood et al., *Nature,* 314:446-449 (1985), all of which are incorporated herein by reference. Antibody fragments such as Fv fragments, single-chain Fv fragments (scFv), Fab' fragments, and $F(ab')_2$ fragments can also be recombinantly produced by methods disclosed in, e.g., U.S. Pat. No. 4,946,778; Skerra & Plückthun, *Science,* 240:1038-1041 (1988); Better et al., *Science,* 240:1041-1043 (1988); and Bird, et al., *Science,* 242:423-426 (1988), all of which are incorporated herein by reference.

In a preferred embodiment, the antibodies provided in accordance with the present invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, *Adv. Immunol.,* 44:65-92 (1989). In addition, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., *Nat. Genetics,* 7: 13-21 (1994); and Lonberg et al., *Nature* 368: 856-859 (1994), all of which are incorporated herein by reference. The transgenic non-human host animal may be immunized with suitable antigens such as a protein variant of the present invention to illicit specific immune response thus producing humanized antibodies. In addition, cell lines producing specific humanized antibodies can also be derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. Alternatively, cDNAs may be extracted from mature B-lymphocytes and used in establishing a library which is subsequently screened for clones encoding humanized antibodies with desired binding specificities.

In a specific embodiment, the antibody is selectively immunoreactive with a variant MYH protein or peptide containing the amino acid variant M15V, R95W, D147H, S167F, R168L, E182X, Q300X, R231H, R231c, Q324R, F344Y, P345T, P391L, A405T, L406M and A475T.

6. Genotyping

The present invention also provides a method for genotyping the MYH gene by determining whether an individual has a nucleotide variant or amino acid variant of the present invention.

Similarly, a method for haplotyping the MYH gene is also provided. Haplotyping can be done by any methods known in the art. For example, only one copy of the MYH gene can be isolated from an individual and the nucleotide at each of the variant positions is determined. Alternatively, an allele specific PCR or a similar method can be used to amplify only one copy of the MYH gene in an individual, and the SNPs at the variant positions of the present invention are determined. The Clark method known in the art can also be employed for haplotyping. A high throughput molecular haplotyping method is also disclosed in Tost et al., *Nucleic Acids Res.,* 30(19):e96 (2002), which is incorporated herein by reference.

Thus, additional variant(s) that are in linkage disequilibrium with the variants and/or haplotypes of the present invention can be identified by a haplotyping method known in the art, as will be apparent to a skilled artisan in the field of genetics and haplotyping. The additional variants that are in linkage disequilibrium with a variant or haplotype of the present invention can also be useful in the various applications as described below.

For purposes of genotyping and haplotyping, both genomic DNA and mRNA/cDNA can be used, and both are herein referred to generically as "gene."

Numerous techniques for detecting nucleotide variants are known in the art and can all be used for the method of this invention. The techniques can be protein-based or DNA-based. In either case, the techniques used must be sufficiently sensitive so as to accurately detect the small nucleotide or amino acid variations. Very often, a probe is utilized which is labeled with a detectable marker. Unless otherwise specified in a particular technique described below, any suitable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., *Nucleic Acids Res.*, 14:6115-6128 (1986); Nguyen et al., *Biotechniques*, 13:116-123 (1992); Rigby et al., *J. Mol. Biol.*, 113:237-251 (1977).

In a DNA-based detection method, target DNA sample, i.e., a sample containing MYH genomic DNA or cDNA or mRNA must be obtained from the individual to be tested. Any tissue or cell sample containing the MYH genomic DNA, mRNA, or cDNA or a portion thereof can be used. For this purpose, a tissue sample containing cell nucleus and thus genomic DNA can be obtained from the individual. Blood samples can also be useful except that only white blood cells and other lymphocytes have cell nucleus, while red blood cells are anucleus and contain only mRNA. Nevertheless, mRNA is also useful as it can be analyzed for the presence of nucleotide variants in its sequence or serve as template for cDNA synthesis. The tissue or cell samples can be analyzed directly without much processing. Alternatively, nucleic acids including the target sequence can be extracted, purified, and/or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

To determine the presence or absence of a particular nucleotide variant, one technique is simply sequencing the target genomic DNA or cDNA, particularly the region encompassing the nucleotide variant locus to be detected. Various sequencing techniques are generally known and widely used in the art including the Sanger method and Gilbert chemical method. The newly developed pyrosequencing method monitors DNA synthesis in real time using a luminometric detection system. Pyrosequencing has been shown to be effective in analyzing genetic polymorphisms such as single-nucleotide polymorphisms and thus can also be used in the present invention. See Nordstrom et al., *Biotechnol. Appl. Biochem.*, 31(2):107-112 (2000); Ahmadian et al., *Anal Biochem.*, 280: 103-110 (2000).

Alternatively, the restriction fragment length polymorphism (RFLP) and AFLP method may also prove to be useful techniques. In particular, if a nucleotide variant in the target MYH DNA results in the elimination or creation of a restriction enzyme recognition site, then digestion of the target DNA with that particular restriction enzyme will generate an altered restriction fragment length pattern. Thus, a detected RFLP or AFLP will indicate the presence of a particular nucleotide variant.

Another useful approach is the single-stranded conformation polymorphism assay (SSCA), which is based on the altered mobility of a single-stranded target DNA spanning the nucleotide variant of interest. A single nucleotide change in the target sequence can result in different intramolecular base pairing pattern, and thus different secondary structure of the single-stranded DNA, which can be detected in a non-denaturing gel. See Orita et al., *Proc. Natl. Acad. Sci. USA*, 86:2776-2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., *Biotechniques*, 5:1016-24 (1999); Sheffield et al., *Am. J. Hum, Genet.*, 49:699-706 (1991); Wartell et al., *Nucleic Acids Res.*, 18:2699-2705 (1990); and Sheffield et al., *Proc. Natl. Acad. Sci. USA*, 86:232-236 (1989). In addition, the double-strand conformation analysis (DSCA) can also be useful in the present invention. See Arguello et al., *Nat. Genet.*, 18:192-194 (1998).

The presence or absence of a nucleotide variant at a particular locus in the MYH gene of an individual can also be detected using the amplification refractory mutation system (ARMS) technique. See e.g., European Patent No. 0,332,435; Newton et al., *Nucleic Acids Res.*, 17:2503-2515 (1989); Fox et al., *Br. J. Cancer*, 77:1267-1274 (1998); Robertson et al., *Eur. Respir. J.*, 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., *Clin. Chem.* 43:1336-1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., *Genomics*, 8:684-692 (1990); Shumaker et al., *Hum. Mutat.*, 7:346-354 (1996); Chen et al., *Genome Res.*, 10:549-547 (2000).

Another set of techniques useful in the present invention is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., *Science*, 241:1077-1080 (1988); Chen et al, *Genome Res.*, 8:549-556 (1998); Iannone et al., *Cytometry*, 39:131-140 (2000). Thus, for example, to detect a single-nucleotide mutation at a particular locus in the MYH gene, two oligonucleotides can be synthesized, one having the MYH sequence just 5' upstream from the locus with its 3' end nucleotide being identical to the nucleotide in the variant locus of the MYH gene, the other having a nucleotide sequence matching the MYH sequence immediately 3' downstream from the locus in the MYH gene. The oligonucleotides can be labeled for the purpose of detection. Upon hybridizing to the target MYH gene under a stringent condition, the two oligonucleotides are subject to ligation in the presence of a suitable ligase. The ligation of the two oligonucleotides would indicate that the target DNA has a nucleotide variant at the locus being detected.

Detection of small genetic variations can also be accomplished by a variety of hybridization-based approaches. Allele-specific oligonucleotides are most useful. See Conner et al., *Proc. Natl. Acad. Sci. USA*, 80:278-282 (1983); Saiki et al, *Proc. Natl. Acad. Sci. USA*, 86:6230-6234 (1989). Oligonucleotide probes (allele-specific) hybridizing specifically to a MYH gene allele having a particular gene variant at a particular locus but not to other alleles can be designed by methods known in the art. The probes can have a length of, e.g., from 10 to about 50 nucleotide bases. The target MYH DNA and the oligonucleotide probe can be contacted with each other under conditions sufficiently stringent such that the nucleotide variant can be distinguished from the wild-type MYH gene based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular nucleotide variant.

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subject to electrophoresis. The mismatched duplexes can be detected based on their electrophoretic mobility that is different from the perfectly matched duplexes. See Cariello, *Human Genetics*, 42:726 (1988). Alternatively, in a RNase protection assay, a RNA probe can be prepared spanning the nucleotide variant site to be detected and having a detection marker. See Giunta et al., *Diagn. Mol. Path.*, 5:265-270 (1996); Finkelstein et al., *Genomics*, 7:167-172 (1990); Kinszler et al., *Science* 251:1366-1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., *Nucleic Acids Res.*, 25:3377-3378 (1997).

In the mutS assay, a probe can be prepared matching the MYH gene sequence surrounding the locus at which the presence or absence of a mutation is to be detected, except that a predetermined nucleotide is used at the variant locus. Upon annealing the probe to the target DNA to form a duplex, the *E. coli* mutS protein is contacted with the duplex. Since the mutS protein binds only to heteroduplex sequences containing a nucleotide mismatch, the binding of the mutS protein will be indicative of the presence of a mutation. See Modrich et al., *Ann. Rev. Genet.*, 25:229-253 (1991).

A great variety of improvements and variations have been developed in the art on the basis of the above-described basic techniques, and can all be useful in detecting mutations or nucleotide variants in the present invention. For example, the "sunrise probes" or "molecular beacons" utilize the fluorescence resonance energy transfer (FRET) property and give rise to high sensitivity. See Wolf et al., *Proc. Nat. Acad. Sci. USA*, 85:8790-8794 (1988). Typically, a probe spanning the nucleotide locus to be detected are designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., *Nucleic Acids Res.*, 25:2516-2521 (1997); Rychlik et al., *Nucleic Acids Res.*, 17:8543-8551 (1989); Sharkey et al., *Bio/Technology* 12:506-509 (1994); Tyagi et al., *Nat. Biotechnol.*, 14:303-308 (1996); Tyagi et al., *Nat. Biotechnol.*, 16:49-53 (1998). The homo-tag assisted non-dimer system (HANDS) can be used in combination with the molecular beacon methods to suppress primer-dimer accumulation. See Brownie et al., *Nucleic Acids Res.*, 25:3235-3241 (1997).

Dye-labeled oligonucleotide ligation assay is a FRET-based method, which combines the OLA assay and PCR. See Chen et al., *Genome Res.* 8:549-556 (1998). TaqMan is another FRET-based method for detecting nucleotide variants. A TaqMan probe can be oligonucleotides designed to have the nucleotide sequence of the MYH gene spanning the variant locus of interest and to differentially hybridize with different MYH alleles. The two ends of the probe are labeled with a quenching fluorophore and a reporter fluorophore, respectively. The TaqMan probe is incorporated into a PCR reaction for the amplification of a target MYH gene region containing the locus of interest using Taq polymerase. As Taq polymerase exhibits 5'-3' exonuclease activity but has no 3'-5' exonuclease activity, if the TaqMan probe is annealed to the target MYH DNA template, the 5'-end of the TaqMan probe will be degraded by Taq polymerase during the PCR reaction thus separating the reporting fluorophore from the quenching fluorophore and releasing fluorescence signals. See Holland et al., *Proc. Natl. Acad. Sci. USA*, 88:7276-7280 (1991); Kalinina et al., *Nucleic Acids Res.*, 25:1999-2004 (1997); Whitcombe et al., *Clin. Chem.*, 44:918-923 (1998).

In addition, the detection in the present invention can also employ a chemiluminescence-based technique. For example, an oligonucleotide probe can be designed to hybridize to either the wild-type or a variant MYH gene locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., *Nucleic Acids Res.*, 24:4998-5003 (1996).

The detection of genetic variation in the MYH gene in accordance with the present invention can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., *Electrophoresis*, 20:1171-1176 (1999).

Another useful technique that is gaining increased popularity is mass spectrometry. See Graber et al., *Curr. Opin. Biotechnol.*, 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., *Nat. Med.,* 3:360-362 (1997).

In addition, the microchip or microarray technologies are also applicable to the detection method of the present invention. Essentially, in microchips, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., *Biotechniques,* 19:442-447 (1995); Chee et al., *Science,* 274:610-614 (1996); Kozal et al., *Nat. Med.* 2:753-759 (1996); Hacia et al., *Nat. Genet.,* 14:441-447 (1996); Saiki et al., *Proc. Natl. Acad. Sci. USA,* 86:6230-6234 (1989); Gingeras et al., *Genome Res.,* 8:435-448 (1998). Alternatively, the multiple target nucleic acid sequences to be studied are fixed onto a substrate and an array of probes is contacted with the immobilized target sequences. See Drmanac et al., *Nat. Biotechnol.,* 16:54-58 (1998). Numerous microchip technologies have been developed incorporating one or more of the above described techniques for detecting mutations. The microchip technologies combined with computerized analysis tools allow fast screening in a large scale. The adaptation of the microchip technologies to the present invention will be apparent to a person of skill in the art apprised of the present disclosure. See, e.g., U.S. Pat. No. 5,925,525 to Fodor et al; Wilgenbus et al., *J. Mol. Med.,* 77:761-786 (1999); Graber et al., *Curr. Opin. Biotechnol.,* 9:14-18 (1998); Hacia et al., *Nat. Genet.,* 14:441-447 (1996); Shoemaker et al., *Nat. Genet.,* 14:450-456 (1996); DeRisi et al., *Nat. Genet.,* 14:457-460 (1996); Chee et al., *Nat. Genet.,* 14:610-614 (1996); Lockhart et al., *Nat. Genet.,* 14:675-680 (1996); Drobyshev et al., *Gene,* 188:45-52 (1997).

As is apparent from the above survey of the suitable detection techniques, it may or may not be necessary to amplify the target DNA, i.e., the MYH gene or cDNA or mRNA to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., *Molecular Cloning: A Laboratory Manual,* $2^{nd}$ ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., *J. Clin. Microbiol.,* 34:901-907 (1996); Collins et al., *Nucleic Acids Res.,* 25:2979-2984 (1997); Horn et al., *Nucleic Acids Res.,* 25:4835-4841 (1997); Horn et al., *Nucleic Acids Res.,* 25:4842-4849 (1997); Nilsen et al., *J. Theor. Biol.,* 187:273-284 (1997).

In yet another technique for detecting single nucleotide variations, the Invader® assay utilizes a novel linear signal amplification technology that improves upon the long turn-around times required of the typical PCR DNA sequenced-based analysis. See Cooksey et al., *Antimicrobial Agents and Chemotherapy* 44:1296-1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The Invader® system utilizes two short DNA probes, which are hybridized to a DNA target. The structure formed by the hybridization event is recognized by a special cleavase enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal. See e.g. Lyamichev et al., *Nat. Biotechnol.,* 17:292-296 (1999).

The rolling circle method is another method that avoids exponential amplification. Lizardi et al., *Nature Genetics,* 19:225-232 (1998) (which is incorporated herein by reference). For example, Sniper™, a commercial embodiment of this method, is a sensitive, high-throughput SNP scoring system designed for the accurate fluorescent detection of specific variants. For each nucleotide variant, two linear, allele-specific probes are designed. The two allele-specific probes are identical with the exception of the 3'-base, which is varied to complement the variant site. In the first stage of the assay, target DNA is denatured and then hybridized with a pair of single, allele-specific, open-circle oligonucleotide probes. When the 3'-base exactly complements the target DNA, ligation of the probe will preferentially occur. Subsequent detection of the circularized oligonucleotide probes is by rolling circle amplification, whereupon the amplified probe products are detected by fluorescence. See Clark and Pickering, *Life Science News* 6, 2000, *Amersham Pharmacia Biotech* (2000).

A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., *Anal. Chem.,* 69:4703-4707 (1997). The fluorescence correlation spectroscopy is based on the spatio-temporal correlations among fluctuating light signals and trapping single molecules in an electric field. See Eigen et al., *Proc. Natl. Acad. Sci. USA,* 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., *Anal. Chem.,* 67:3181-3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the present invention for detecting the presence or absence of a nucleotide variant in the MYH gene of a particular individual should be apparent to a skilled artisan apprised of this disclosure.

Protein-based detection techniques may also prove to be useful, especially when the nucleotide variant causes amino acid substitutions or deletions or insertions or frameshift that affect the protein primary, secondary or tertiary structure. To detect the amino acid variations, protein sequencing techniques may be used. For example, an MYH protein or fragment thereof can be synthesized by recombinant expression using an MYH DNA fragment isolated from an individual to be tested. Preferably, an MYH cDNA fragment of no more than 100 to 150 base pairs encompassing the polymorphic locus to be determined is used. The amino acid sequence of the peptide can then be determined by conventional protein sequencing methods. Alternatively, the recently developed HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., *Anal. Chem.*, 72:757-763 (2000).

Other useful protein-based detection techniques include immunoaffinity assays based on antibodies selectively immunoreactive with mutant MYH proteins according to the present invention. The method for producing such antibodies is described above in detail. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well-known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

Accordingly, the presence or absence of an MYH nucleotide variant or amino acid variant in an individual can be determined using any of the detection methods described above.

Typically, once the presence or absence of an MYH nucleotide variant or an amino acid variant resulting from a nucleotide variant of the present invention is determined, physicians or genetic counselors or patients or other researchers may be informed of the result. Specifically the result can be cast in a transmittable form that can be communicated or transmitted to other researchers or physicians or genetic counselors or patients. Such a form can vary and can be tangible or intangible. The result with regard to the presence or absence of a MYH nucleotide variant of the present invention in the individual tested can be embodied in descriptive statements, diagrams, photographs, charts, images or any other visual forms. For example, images of gel electrophoresis of PCR products can be used in explaining the results. Diagrams showing where a variant occurs in an individual's MYH gene are also useful in indicating the testing results. The statements and visual forms can be recorded on a tangible media such as papers, computer readable media such as floppy disks, compact disks, etc., or on an intangible media, e.g., an electronic media in the form of email or website on internet or intranet. In addition, the result with regard to the presence or absence of a nucleotide variant or amino acid variant of the present invention in the individual tested can also be recorded in a sound form and transmitted through any suitable media, e.g., analog or digital cable lines, fiber optic cables, etc., via telephone, facsimile, wireless mobile phone, internet phone and the like.

Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present invention also encompasses a method for producing a transmittable form of information on the MYH genotype of an individual. The method comprises the steps of (1) determining the presence or absence of a nucleotide variant according to the present invention in the MYH gene of the individual; and (2) embodying the result of the determining step in a transmittable form. The transmittable form is the product of the production method.

The present invention also provides a kit for genotyping MYH gene, i.e., determining the presence or absence of one or more of the nucleotide or amino acid variants of present invention in a MYH gene in a sample obtained from a patient. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit also includes various components useful in detecting nucleotide or amino acid variants discovered in accordance with the present invention using the above-discussed detection techniques.

In one embodiment, the detection kit includes one or more oligonucleotides useful in detecting one or more of the nucleotide variants in MYH gene. Preferably, the oligonucleotides are allele-specific, i.e., are designed such that they hybridize only to a mutant MYH gene containing a particular nucleotide variant discovered in accordance with the present invention, under stringent conditions. Thus, the oligonucleotides can be used in mutation-detecting techniques such as allele-specific oligonucleotides (ASO), allele-specific PCR, TaqMan, chemiluminescence-based techniques, molecular beacons, and improvements or derivatives thereof, e.g., microchip technologies. The oligonucleotides in this embodiment preferably have a nucleotide sequence that matches a nucleotide sequence of a variant MYH gene allele containing a nucleotide variant to be detected. The length of the oligonucleotides in accordance with this embodiment of the invention can vary depending on its nucleotide sequence and the hybridization conditions employed in the detection procedure. Preferably, the oligonucleotides contain from about 10 nucleotides to about 100 nucleotides, more preferably from about 15 to about 75 nucleotides, e.g., contiguous span of 18, 19, 20, 21, 22, 23, 24 or 25 to 21, 22, 23, 24, 26, 27, 28, 29 or 30 nucleotide residues of a MYH nucleic acid one or more of the residues being a nucleotide variant of the present invention, i.e., selected from Table 1. Under most conditions, a length of 18 to 30 may be optimum. In any event, the oligonucleotides should be designed such that it can be used in distinguishing one nucleotide variant from another at a particular locus under predetermined stringent hybridization conditions. Preferably, a nucleotide variant is located at the center or within one (1) nucleotide of the center of the oligonucleotides, or at the 3' or 5' end of the oligonucleotides. The hybridization of an oligonucleotide with a nucleic acid and the optimization of the length and hybridization conditions should be apparent to a person of skill in the art. See generally, Sambrook et al., *Molecular Cloning: A Laboratory Manual*, $2^{nd}$ ed., Cold Spring Harbor Laboratory, Cold Spring Harbor, N.Y., 1989. Notably, the oligonucleotides in accordance with this embodiment are also useful in mismatch-based detection techniques described above, such as electrophoretic mobility shift assay, RNase protection assay, mutS assay, etc.

In another embodiment of this invention, the kit includes one or more oligonucleotides suitable for use in detecting techniques such as ARMS, oligonucleotide ligation assay (OLA), and the like. The oligonucleotides in this embodiment include a MYH gene sequence of about 10 to about 100 nucleotides, preferably from about 15 to about 75 nucleotides, e.g., contiguous span of 18, 19, 20, 21, 22, 23, 24 or 25 to 21, 22, 23, 24, 26, 27, 28, 29 or 30 nucleotide residues immediately 5' upstream from the nucleotide variant to be analyzed. The 3' end nucleotide in such oligonucleotides is a nucleotide variant in accordance with this invention.

The oligonucleotides in the detection kit can be labeled with any suitable detection marker including but not limited to, radioactive isotopes, fluorephores, biotin, enzymes (e.g., alkaline phosphatase), enzyme substrates, ligands and antibodies, etc. See Jablonski et al., *Nucleic Acids Res.*, 14:6115-6128 (1986); Nguyen et al., *Biotechniques*, 13:116-123 (1992); Rigby et al., *J. Mol. Biol.*, 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies selectively immunoreactive with certain MYH proteins or polypeptides containing specific amino acid variants discovered in the present invention. Methods for producing and using such antibodies have been described above in detail.

Various other components useful in the detection techniques may also be included in the detection kit of this invention. Examples of such components include, but are not limited to, Taq polymerase, deoxyribonucleotides, dideoxyribonucleotides other primers suitable for the amplification of a target DNA sequence, RNase A, mutS protein, and the like. In addition, the detection kit preferably includes instructions on using the kit for detecting nucleotide variants in MYH gene sequences.

7. Use of Genotyping in Diagnosis Applications

The present invention further relates to methods of determining in and individual predisposition to cancer, especially colorectal cancer. As indicated above, the present invention provides MYH polymorphisms associated with cancer, especially colorectal cancer. Specifically, the polymorphisms 43A→G, 225C→T, 283C→T, 544G→T, 898C→T, IVS13+25del30, IVS12-2A→G, 439G→C, 503G→C, 1172C→T, 1213G→A, 1423G→A, 971A→G, 1031T→A, 1033C→A, 1216C→A, 500C→T, 423G→A, 1506G→A, 691C→T, 692G→A and IVS6-4 A→G are associated with predisposition to cancer, especially colorectal cancer. Thus, the polymorphisms disclosed herein are particularly useful in predicting predisposition to cancer in an individual.

Thus, in one aspect, the present invention encompasses a method for predicting or detecting cancer susceptibility in an individual, which comprises the step of genotyping the individual to determine the individual's genotype at one or more of the loci identified in the present invention, or another locus at which the genotype is in linkage disequilibrium with one of the polymorphisms of the present invention. Thus, if one or more of the polymorphisms 43A→G, 225C→T, 283C→T, 544G→T, 898C→T, IVS13+25del30, IVS12-2A→G, 439G→C, 503G→C, 1172C→T, 1213G→A, 1423G→A, 971A→G, 1031T→A, 1033C→A, 1216C→A, 500C→T, 423G→A, 1506G→A, 691C→T, 692G→A or IVS6-4 A→G is detected then it can be reasonably predicted that the individual is at an increased risk of developing cancer, particularly colon cancer. In particular, if an individual is homozygous with the genotype 43A→G, 225C→T, 283C→T, 544G→T, 898C→T, IVS13+25del30, IVS12-2A→G, 439G→C, 503G→C, 1172C→T, 1213G→A, 1423G→A, 971A→G, 1031T→A, 1033C→A, 1216C→A, 500C→T, 423G→A, 1506G→A, 691C→T, 692G→A and IVS6-4 A→G is detected then it can be reasonably predicted that the individual has a high susceptibility to cancer, particularly colon cancer. In other words, such an individual has an increased likelihood or is at an increased risk of developing cancer, particularly colon cancer. If an individual is heterozygous for one or more of the genetic variants (e.g., 43A→G, 225C→T, 283C→T, 544G→T, 898C→T, IVS13+25del30, IVS12-2A→G, 439G→C, 503G→C, 1172C→T, 1213G→A, 1423G→A, 971A→G, 1031T→A, 1033C→A, 1216C→A, 500C→T, 423G→A, 1506G→A, 691C→T, 692G→A and IVS6-4 A→G) then his or her risk of developing cancer is at an intermediate level. On the other hand, if one or more of the genetic variants of the present invention, or those previously known to be associated with predisposition to cancer, (e.g., 43A→G, 225C→T, 283C→T, 544G→T, 898C→T, IVS13+25del30, IVS12-2A→G, 439G→C, 503G→C, 1172C→T, 1213G→A, 1423G→A, 971A→G, 1031T→A, 1033C→A, 1216C→A, 500C→T, 423G→A, 1506G→A, 691C→T, 692G→A and IVS6-4 A→G) is not detected in the individual, then it can be reasonably predicted that the individual has a low susceptibility to cancer, particularly colon cancer.

8. Screening Assays

The present invention further provides a method for identifying compounds for treating or preventing symptoms amendable to treatment by alteration of MYH protein activities. For this purpose, variant MYH protein or fragment thereof containing a particular amino acid variant in accordance with the present invention can be used in any of a variety of drug screening techniques. Drug screening can be performed as described herein or using well known techniques, such as those described in U.S. Pat. Nos. 5,800,998 and 5,891,628, both of which are incorporated herein by reference. The candidate therapeutic compounds may include, but are not limited to proteins, small peptides, nucleic acids, and analogs thereof. Preferably, the compounds are small organic molecules having a molecular weight of no greater than 10,000 dalton, more preferably less than 5,000 dalton.

In one embodiment of the present invention, the method is primarily based on binding affinities to screen for compounds capable of interacting with or binding to a MYH protein containing one or more amino acid variants. Compounds to be screened may be peptides or derivatives or mimetics thereof, or non-peptide small molecules. Conveniently, commercially available combinatorial libraries of compounds or phage display libraries displaying random peptides are used.

Various screening techniques known in the art may be used in the present invention. The MYH protein variants (drug target) can be prepared by any suitable methods, e.g., by recombinant expression and purification. The polypeptide or fragment thereof may be free in solution but preferably is immobilized on a solid support, e.g., in a protein microchip, or on a cell surface. Various techniques for immobilizing proteins on a solid support are known in the art. For example, PCT Publication WO 84/03564 discloses synthesizing a large numbers of small peptide test compounds on a solid substrate, such as plastic pins or other surfaces. Alternatively, purified mutant MYH protein or fragment thereof can be coated directly onto plates such as multi-well plates. Non-neutralizing antibodies, i.e., antibodies capable binding to the MYH protein or fragment thereof but do not substantially affect its biological activities may also be used for immobilizing the MYH protein or fragment thereof on a solid support.

To effect the screening, test compounds can be contacted with the immobilized MYH protein or fragment thereof to allow binding to occur to form complexes under standard binding assays. Either the drug target or test compounds are labeled with a detectable marker using well known labeling techniques. To identify binding compounds, one may measure the formation of the drug target-test compound complexes or kinetics for the formation thereof.

Alternatively, a known ligand capable of binding to the drug target can be used in competitive binding assays. Complexes between the known ligand and the drug target can be formed and then contacted with test compounds. The ability of a test compound to interfere with the interaction between the drug target and the known ligand is measured using known techniques. One exemplary ligand is an antibody capable of specifically binding the drug target. Particularly, such an antibody is especially useful for identifying peptides that share one or more antigenic determinants of the MYH protein or fragment thereof.

In another embodiment, a yeast two-hybrid system may be employed to screen for proteins or small peptides capable of interacting with a MYH protein variant. For example, a battery of fusion proteins each contains a random small peptide fused to e.g., Gal 4 activation domain, can be co-expressed in yeast cells with a fusion protein having the Gal 4 binding domain fused to a MYH protein variant. In this manner, small peptides capable of interacting with the MYH protein variant can be identified. Alternatively, compounds can also be tested in a yeast two-hybrid system to determine their ability to inhibit the interaction between the MYH protein variant and a known protein capable of interacting with the MYH protein or polypeptide or fragment thereof. Again, one example of such proteins is an antibody specifically against the MYH protein variant. Yeast two-hybrid systems and use thereof are generally known in the art and are disclosed in, e.g., Bartel et al., in: *Cellular Interactions in Development: A Practical Approach*, Oxford University Press, pp. 153-179 (1993); Fields and Song, *Nature*, 340:245-246 (1989); Chevray and Nathans, *Proc. Natl. Acad. Sci. USA*, 89:5789-5793 (1992); Lee et al., *Science*, 268:836-844 (1995); and U.S. Pat. Nos. 6,057,101, 6,051,381, and 5,525,490, all of which are incorporated herein by reference.

The compounds thus identified can be further tested for activities, e.g., in stimulating the variant MYH's biological activities, e.g., in DNA mismatch repair.

Once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., *Bio/Technology*, 9:19-21 (1991); U.S. Pat. Nos. 5,800,998 and 5,891,628, all of which are incorporated herein by reference. An example of rational drug design is the development of HIV protease inhibitors. See Erickson et al., *Science*, 249:527-533 (1990). Preferably, rational drug design is based on one or more compounds selectively binding to a variant MYH protein or a fragment thereof.

In one embodiment, the three-dimensional structure of, e.g., a MYH protein variant, is determined by biophysics techniques such as X-ray crystallography, computer modeling, or both. Desirably, the structure of the complex between an effective compound and the variant MYH protein is determined, and the structural relationship between the compound and the protein is elucidated. In this manner, the moieties and the three-dimensional structure of the selected compound, i.e., lead compound, critical to the its binding to the variant MYH protein are revealed. Medicinal chemists can then design analog compounds having similar moieties and structures. In addition, the three-dimensional structure of wild-type MYH protein is also desirably deciphered and compared to that of a variant MYH protein. This will aid in designing compounds selectively interacting with the variant MYH protein.

In another approach, a selected peptide compound capable of binding the MYH protein variant can be analyzed by an alanine scan. See Wells, et al., *Methods Enzymol.*, 202:301-306 (1991). In this technique, an amino acid residue of the peptide is replaced by Alanine, and its effect on the peptide's binding affinity to the variant MYH protein is tested. Amino acid residues of the selected peptide are analyzed in this manner to determine the domains or residues of the peptide important to its binding to variant MYH protein. These residues or domains constituting the active region of the compound are known as its "pharmacophore." This information can be very helpful in rationally designing improved compounds.

Once the pharmacophore has been elucidated, a structural model can be established by a modeling process which may include analyzing the physical properties of the pharmacophore such as stereochemistry, charge, bonding, and size using data from a range of sources, e.g., NMR analysis, x-ray diffraction data, alanine scanning, and spectroscopic techniques and the like. Various techniques including computational analysis, similarity mapping and the like can all be used in this modeling process. See e.g., Perry et al., in *OSAR: Quantitative Structure-Activity Relationships in Drug Design*, pp. 189-193, Alan R. Liss, Inc., 1989; Rotivinen et al., *Acta Pharmaceutical Fennica*, 97:159-166 (1988); Lewis et al., *Proc. R. Soc. Lond.*, 236:125-140 (1989); McKinaly et al., *Annu. Rev. Pharmacol. Toxiciol.*, 29:111-122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed.

9. Cell and Animal Models

In yet another aspect of the present invention, a cell line and a transgenic animal carrying an MYH gene containing one or more of the nucleotide variants in accordance with the present invention are provided. The cell line and transgenic animal can be used as a model system for studying cancers and testing various therapeutic approaches in treating cancers.

To establish the cell line, cells expressing the variant MYH protein can be isolated from an individual carrying the nucleotide variants. The primary cells can be transformed or immortalized using techniques known in the art. Alternatively, normal cells expressing a wild-type MYH protein or other type of nucleotide variants can be manipulated to replace the entire endogenous MYH gene with a variant MYH gene containing one or more of the nucleotide variants in accordance with the present invention, or simply to introduce mutations into the endogenous MYH gene. The genetically engineered cells can further be immortalized.

A more valuable model system is a transgenic animal. A transgenic animal can be made by replacing the endogenous animal MYH gene with a variant MYH gene containing one or more of the nucleotide variants in accordance with the present invention. Alternatively, insertions and/or deletions can be introduced into the endogenous animal MYH gene to simulate the MYH alleles discovered in accordance with the present invention. Techniques for making such transgenic animals are well known and are described in, e.g., Capecchi, et al., *Science*, 244:1288 (1989); Hasty et al., *Nature*, 350:243 (1991); Shinkai et al., *Cell*, 68:855 (1992); Mombaerts et al., *Cell*, 68:869 (1992); Philpott et al., *Science*, 256:1448 (1992); Snouwaert et al., *Science*, 257:1083 (1992); Donehower et al., *Nature*, 356:215 (1992); Hogan et al., *Manipulating the Mouse Embryo; A Laboratory Manual*, $2^{nd}$ edition, Cold Spring Harbor Laboratory Press, 1994; and U.S. Pat. Nos. 5,800,998, 5,891,628, and 4,873,191, all of which are incorporated herein by reference.

The cell line and transgenic animal are valuable tools for studying the variant MYH genes, and in particular for testing in vivo the compounds identified in the screening method of this invention and other therapeutic approaches as discussed below. As is known in the art, studying drug candidates in a suitable animal model before advancing them into human clinical trials is particularly important because efficacy of the drug candidates can be confirmed in the model animal, and the toxicology profiles, side effects, and dosage ranges can be determined. Such information is then used to guide human clinical trials.

10. Therapeutic Applications

As discussed above, the MYH protein variants provided in accordance with the present invention are likely to be defective in activities in DNA mismatch repair system and can be associated with increased likelihood of developing cancer, e.g., colorectal. Thus, once an individual is identified as having one of such variants and is determined to have or be predisposed to cancer (as determined by the methods provided in the present invention), the individual can be placed under prophylactic or therapeutic treatment.

In one embodiment, a normal or wild-type MYH protein may be administered directly to the patient. For this purpose, the normal or wild-type MYH protein may be prepared by any one of the methods described in Section 4 may be administered to the patient, preferably in a pharmaceutical composition as described below. Proteins isolated or purified from normal individuals or recombinantly produced can all be used in this respect.

In another embodiment, gene therapy approaches are employed to supply functional MYH proteins to a patient in need of treatment. For example, a nucleic acid encoding a normal or wild-type MYH protein may be introduced into tissue cells of a patient such that the protein is expressed from the introduced nucleic acids. The exogenous nucleic acid can be used to replace the corresponding endogenous defective gene by, e.g., homologous recombination. See U.S. Pat. No. 6,010,908, which is incorporated herein by reference. Alternatively, if the disease-causing mutation is a recessive mutation, the exogenous nucleic acid is simply used to express a wild-type protein in addition to the endogenous mutant protein. In another approach, the method disclosed in U.S. Pat. No. 6,077,705 may be employed in gene therapy. That is, the patient is administered both a nucleic acid construct encoding a ribozyme and a nucleic acid construct comprising a ribozyme resistant gene encoding a wild type form of the gene product. As a result, undesirable expression of the endogenous gene is inhibited and a desirable wild-type exogenous gene is introduced.

Various gene therapy methods are well known in the art. Successes in gene therapy have been reported recently. See e.g., Kay et al., *Nature Genet.*, 24:257-61 (2000); Cavazzana-Calvo et al., *Science*, 288:669 (2000); and Blaese et al., *Science*, 270: 475 (1995); Kantoff, et al., *J. Exp. Med.* 166:219 (1987).

Any suitable gene therapy methods can be used for purposes of the present invention. Generally, a nucleic acid encoding a desirable functional MYH protein is incorporated into a suitable expression vector and is operably linked to a promoter in the vector. Suitable promoters include but are not limited to viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Where tissue-specific expression of the exogenous gene is desirable, tissue-specific promoters may be operably linked to the exogenous gene. In addition, selection markers may also be included in the vector for purposes of selecting, in vitro, those cells that contain the exogenous gene. Various selection markers known in the art may be used including, but not limited to, e.g., genes conferring resistance to neomycin, hygromycin, zeocin, and the like.

In one embodiment, the exogenous nucleic acid (gene) is incorporated into a plasmid DNA vector. Many commercially available expression vectors may be useful for the present invention, including, e.g., pCEP4, pcDNAI, pIND, pSecTag2, pVAX1, pcDNA3.1, and pBI-EGFP, and pDisplay.

Various viral vectors may also be used. Typically, in a viral vector, the viral genome is engineered to eliminate the disease-causing capability, e.g., the ability to replicate in the host cells. The exogenous nucleic acid to be introduced into a patient may be incorporated into the engineered viral genome, e.g., by inserting it into a viral gene that is non-essential to the viral infectivity. Viral vectors are convenient to use as they can be easily introduced into tissue cells by way of infection. Once in the host cell, the recombinant virus typically is integrated into the genome of the host cell. In rare instances, the recombinant virus may also replicate and remain as extrachromosomal elements.

A large number of retroviral vectors have been developed for gene therapy. These include vectors derived from oncoretroviruses (e.g., MLV), lentiviruses (e.g., HIV and SIV) and other retroviruses. For example, gene therapy vectors have been developed based on murine leukemia virus (See, Cepko, et al., *Cell*, 37:1053-1062 (1984), Cone and Mulligan, *Proc. Natl. Acad. Sci. U.S.A.*, 81:6349-6353 (1984)), mouse mammary tumor virus (See, Salmons et al., *Biochem. Biophys.*

*Res. Commun.*, 159: 1191-1198 (1984)), gibbon ape leukemia virus (See, Miller et al., *J. Virology*, 65:2220-2224 (1991)), HIV, (See Shimada et al., *J. Clin. Invest.*, 88:1043-1047 (1991)), and avian retroviruses (See Cosset et al., *J. Virology*, 64:1070-1078 (1990)). In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference.

Adeno-associated virus (AAV) vectors have been successfully tested in clinical trials. See e.g., Kay et al., *Nature Genet.* 24:257-61 (2000). AAV is a naturally occurring defective virus that requires other viruses such as adenoviruses or herpes viruses as helper viruses. See Muzyczka, *Curr. Top. Microbiol. Immun.*, 158:97 (1992). A recombinant AAV virus useful as a gene therapy vector is disclosed in U.S. Pat. No. 6,153,436, which is incorporated herein by reference.

Adenoviral vectors can also be useful for purposes of gene therapy in accordance with the present invention. For example, U.S. Pat. No. 6,001,816 discloses an adenoviral vector, which is used to deliver a leptin gene intravenously to a mammal to treat obesity. Other recombinant adenoviral vectors may also be used, which include those disclosed in U.S. Pat. Nos. 6,171,855; 6,140,087; 6,063,622; 6,033,908; and 5,932,210, and Rosenfeld et al., *Science*, 252:431-434 (1991); and Rosenfeld et al., Cell, 68:143-155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258).

Other non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or uptaken by cells.

The exogenous gene fragment or plasmid DNA vector containing the exogenous gene may also be introduced into cells by way of receptor-mediated endocytosis. See e.g., U.S. Pat. No. 6,090,619; Wu and Wu, *J. Biol. Chem.*, 263:14621 (1988); Curiel et al., *Proc. Natl. Acad. Sci. USA*, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor binding moiety (e.g., a cyclic peptide having the sequence RGD).

Alternatively, the exogenous nucleic acid or vectors containing it can also be delivered into cells via amphiphiles. See e.g., U.S. Pat. No. 6,071,890. Typically, the exogenous nucleic acid or a vector containing the nucleic acid forms a complex with the cationic amphiphile. Mammalian cells contacted with the complex can readily take the complex up.

The exogenous gene can be introduced into a patient for purposes of gene therapy by various methods known in the art. For example, the exogenous gene sequences alone or in a conjugated or complex form described above, or incorporated into viral or DNA vectors, may be administered directly by injection into an appropriate tissue or organ of a patient. Alternatively, catheters or like devices may be used for delivery into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

In addition, the exogenous gene or vectors containing the gene can be introduced into isolated cells using any known techniques such as calcium phosphate precipitation, microinjection, lipofection, electroporation, gene gun, receptor-mediated endocytosis, and the like. Cells expressing the exogenous gene may be selected and redelivered back to the patient by, e.g., injection or cell transplantation. The appropriate amount of cells delivered to a patient will vary with patient conditions, and desired effect, which can be determined by a skilled artisan. See e.g., U.S. Pat. Nos. 6,054,288; 6,048,524; and 6,048,729. Preferably, the cells used are autologous, i.e., cells obtained from the patient being treated.

In another embodiment of the present invention, a compound capable of activating the endogenous MYH protein can be administered to a patient in need of treatment for prophylactic or therapeutic purposes. The compound can be used in stimulate the cellular functions and activities of MYH. For example, compounds identified in the screen assays in Section 7 can be used.

11. Pharmaceutical Compositions and Formulations

In another aspect of the present invention, pharmaceutical compositions are also provided containing one or more of the therapeutic agents provided in the present invention. The compositions are prepared as a pharmaceutical formulation suitable for administration into a patient. Accordingly, the present invention also extends to pharmaceutical compositions, medicaments, drugs or other compositions containing one or more of the therapeutic agent in accordance with the present invention.

In the pharmaceutical composition, an active compound identified in accordance with the present invention can be in any pharmaceutically acceptable salt form. As used herein, the term "pharmaceutically acceptable salts" refers to the relatively non-toxic, organic or inorganic salts of the compounds of the present invention, including inorganic or organic acid addition salts of the compound. Examples of such salts include, but are not limited to, hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like. See, e.g., Berge, et al., *J. Pharm. Sci.*, 66:1-19 (1977).

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and anti-oxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine*, 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych*. 45:242-247 (1984). Hydrogels can be used as a carrier for the sustained release of the active compounds. Hydrogels are generally known in the art. They are typically made by cross-linking high molecular weight biocompatible polymers into a network, which swells in water to form a gel like material. Preferably, hydrogels is biodegradable or biosorbable. For purposes of this invention, hydrogels made of polyethylene glycols, collagen, or poly (glycolic-co-L-lactic acid) may be useful. See, e.g., Phillips et al., *J. Pharmaceut. Sci*. 73:1718-1720 (1984).

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm.*, 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology*, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, anti-thrombotic agents, cardiovascular drugs, cholesterol lowering agents, hypertension drugs, and other anti-cancer drugs, and the like.

Generally, the toxicity profile and therapeutic efficacy of the therapeutic agents can be determined by standard pharmaceutical procedures in cell models or animal models, e.g., those provided in Section 7. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the $ED_{50}$ and/or $IC_{50}$, but significantly below the $LD_{50}$ obtained from cell or animal models.

It will be apparent to skilled artisans that therapeutically effective amount for each active compound to be included in a pharmaceutical composition of the present invention can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like. The amount of administration can also be adjusted as the various factors change over time.

Example 1

Identification of MYH Variants

Twelve PCR reactions were used to amplify the patient's DNA from the coding regions of MYH. The PCR products were sequenced in the forward and reverse directions using fluorescent dye-labeled sequencing primers. Chromatographic tracings of each amplicon were analyzed by visual inspection and computer software designed to analyze such traces. Analysis of the DNA sequences indicated the presence of the following mutation.

Novel mutations and variants detected in APC negative patient samples:
  Truncating Mutations
    E182X (544G→T)
    Q300X (898 C→T)
  Deletion Mutations
    IVS13+25del30
  Splice Mutations
    IVS12-2A→G
  Missense Variants
    D147H (439 G→C)
    R168L (503 G→C)
    P391L (1172 C→T)
    A405T (1213 G→A)
    A475T (1423 G→A)
  Translationally Silent Variants
    D75D (225 C→T)

Novel missense variants detected in HNPCC negative patient samples:
  M15V (43 A→G)
  Q324R (971 A→G)
  F344Y (1031 T→A)
  P345T (1033 C→A)
  L406M (1216 C→A)

Novel Missense Variant
  R231C (691 C→T)

Example 2

Whole-Gene Screening for MYH Mutations

209 APC negative colorectal cancer patient specimens were tested for previously identified MYH mutations Y165C and G382D. Testing revealed 13 biallelic mutations and 15 heterozygous mutations among the initial 209 samples. Whole-gene mutation screening of the 15 heterozygous samples revealed that 9 carried a second mutation. Thus, 24 of the total 219 specimens (11.0%) screened were biallelic (e.g. carried a second mutation). Further, 306 HNPCC negative colorectal cancer patient specimens found negative for MLH1 and MSH2 were screened for Y165C and G382D MYH mutations. 4.25% were found to have MYH mutation, 3 of which were biallelic.

Comparison of the results for the number of Y165C and G382D mutations in the HNPCC negative group with the control group indicated a statistically significant difference with a p value <0.05. Furthermore, there was a significant difference between the number of second mutations found after full sequencing of the heterozygotes in the APC negative group versus the HNPCC negative group (p=0.008).

Logistic regression was used to model the effect of MYH mutations on case/control status. The MYH explanatory variable is the combined number of G382D and Y165C mutations (0, 1, or 2). The sample included 306 cases that were negative for colorectal cancer associated genes MLH1 and MSH2 in clinical tests, and 497 controls. Statistical analysis was performed using S-PLUS v. 6.2.1 for Unix/Linux (Insightful Corp., Seattle, Wash.). The likelihood ratio test yielded a two-sided p-value of 0.0270, indicating that the MYH effect is significant at a level of 0.05.

The number of heterozygote specimens (G382D/WT or Y156C/WT) that were shown by full sequencing to have another variant was also compared in the two case samples. The odds ratio of APC negative/HNPCC negative individuals is 13.5.

TABLE 2

Presence of Second Genomic Variant in APC and HNPCC Negative Patients

| | APC Negative Patients | HNPCC Negative Patients |
|---|---|---|
| Biallelic | 9 | 1 |
| Single Polymorphism | 6 | 9 |

Example 2

Generation of Genotype Data

A patient's DNA sample was analyzed for mutations in the MYH gene. A heterozygous Y165C mutation was found upon sequencing for the most common lesions in MYH. Full-length gene sequencing encompassing the 16 exons of MYH as well as the exon/intron boundaries was performed and another mutation was found in at nucleotide position 692 (G→A) corresponding to an R231H amino acid change.

While there may be alternatively spliced variants of gene transcripts, the exon and intron numbering and the SNP positions of the present invention would be clearly understood by a skilled artisan by reference to the sequences in the sequence listing together with GenBank Accession No. NT_032977 (PRI 19-AUG-2004) or a variant or modification of this GenBank sequence. However, it is noted that the polymorphisms of the present invention are by no means limited to be only in the context of the sequences in the sequence listings or the particular GenBank entry referred to herein. Rather, it is recognized that GenBank sequences may contain unrecognized sequence errors only to be corrected at a later date, and additional gene variants may be discovered in the future. The present invention encompasses SNPs or nucleotide variants as referred to in Table 1 irrespective of such sequence contexts. Indeed, even if the GenBank entries referred to herein are changed based on either error corrections or additional variants discovered, skilled artisans apprised of the present disclosure would still be able to determine or analyze the SNPs or haplotypes of the present invention in the new sequence contexts.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for genotyping an individual comprising: detecting the 691C→T nucleotide variant in an MYH gene obtained from said individual.

2. The method of claim 1, wherein said detecting step comprises sequencing the MYH gene.

3. The method of claim 1, wherein a nucleic acid comprising said nucleotide variant is amplified from genomic DNA.

4. The method of claim 1, wherein said detecting step comprises DNA sequence analysis of the MYH gene.

5. The method of claim 1, wherein said detecting step comprises amplifying an exon, or fragment thereof, corresponding to the 691C→T nucleotide variant.

6. The method of claim 1, wherein said MYH gene of said individual is examined for other MYH variants.

7. The method of claim 1, further comprising embodying results of said detecting step in a transmittable form.

8. A method for determining an increased likelihood for developing colon cancer in an individual, comprising: determining from a sample obtained from said individual whether said individual has the 691C→T nucleotide variant in an MYH gene of said individual, wherein the presence of said nucleotide variant is indicative of an increased likelihood for developing colon cancer.

9. The method of claim 8, wherein said determining step comprises sequencing the MYH gene.

10. The method of claim 8, wherein said determining step comprises amplifying the nucleotide variant from genomic DNA.

11. The method of claim 8, wherein said sample comprises genomic DNA.

12. The method of claim 8, wherein said determining step comprises amplifying an exon, or fragment thereof, corresponding to the 691C→T nucleotide variant.

13. The method of claim 8, wherein said MYH gene of said individual is examined for other MYH variants.

14. The method of claim 8, further comprising embodying results of said determining step in a transmittable form.

* * * * *